(12) United States Patent
Xu et al.

(10) Patent No.: US 10,894,076 B2
(45) Date of Patent: Jan. 19, 2021

(54) COMPOSITION COMPRISING GLP-1 RECEPTOR AGONIST AND GLUCAGON RECEPTOR AGONIST AND APPLICATION THEREOF

(71) Applicant: PEGBIO CO., LTD., Jiangsu (CN)

(72) Inventors: Michael Min Xu, Jiangsu (CN); Wei Lv, Jiangsu (CN); Yinghui Zhang, Jiangsu (CN); Xiaosu Luo, Jiangsu (CN)

(73) Assignee: PEGBIO CO., LTD., Juangsu (CN)

( * ) Notice: Subject to any disclaimer, the term of this patent is extended or adjusted under 35 U.S.C. 154(b) by 63 days.

(21) Appl. No.: 16/066,586

(22) PCT Filed: Dec. 28, 2016

(86) PCT No.: PCT/CN2016/112674
§ 371 (c)(1),
(2) Date: Jun. 27, 2018

(87) PCT Pub. No.: WO2017/114425
PCT Pub. Date: Jul. 6, 2017

(65) Prior Publication Data
US 2019/0134161 A1    May 9, 2019

(30) Foreign Application Priority Data

Dec. 29, 2015    (CN) .......................... 2015 1 1017796

(51) Int. Cl.
| A61K 38/26 | (2006.01) |
| A61K 38/17 | (2006.01) |
| A61K 45/06 | (2006.01) |
| A61K 47/60 | (2017.01) |
| A61P 3/04 | (2006.01) |
| A61P 3/06 | (2006.01) |
| A61P 3/10 | (2006.01) |

(52) U.S. Cl.
CPC ............. *A61K 38/26* (2013.01); *A61K 38/17* (2013.01); *A61K 45/06* (2013.01); *A61K 47/60* (2017.08); *A61P 3/04* (2018.01); *A61P 3/06* (2018.01); *A61P 3/10* (2018.01)

(58) Field of Classification Search
CPC .................................................... A61K 38/26
See application file for complete search history.

(56) References Cited

U.S. PATENT DOCUMENTS

| 8,546,327 B2 | 10/2013 | Dimarchi et al. |
| 8,575,097 B2 * | 11/2013 | Xu ........................ A61K 47/60 514/7.2 |
| 10,172,953 B2 | 1/2019 | Schellenberger et al. |
| 2010/0190701 A1 | 7/2010 | Day et al. |
| 2010/0323956 A1 | 12/2010 | Schellenberger et al. |
| 2011/0190200 A1 | 8/2011 | DiMarchi et al. |
| 2012/0196795 A1 | 8/2012 | Xu et al. |
| 2012/0329708 A1 | 12/2012 | DiMarchi et al. |
| 2013/0122023 A1 | 5/2013 | Woo et al. |
| 2013/0137645 A1 | 5/2013 | Rosendahl |
| 2013/0217622 A1 | 8/2013 | Lee et al. |
| 2014/0206608 A1 | 7/2014 | Haack et al. |
| 2014/0349922 A1 | 11/2014 | Fima et al. |
| 2015/0307579 A1 | 10/2015 | Agoram et al. |

FOREIGN PATENT DOCUMENTS

| CN | 103338790 | 2/2013 |
| CN | 104822699 | 8/2015 |
| CN | 104902920 | 9/2015 |
| EP | 2423223 | 2/2012 |
| JP | 2011524419 A | 9/2011 |
| JP | 2012529297 | 11/2012 |
| JP | 2013537525 A | 10/2013 |
| KR | 10-2009-0119876 A | 11/2009 |
| WO | WO2009155257 | 12/2009 |
| WO | WO2012012352 A2 | 1/2012 |
| WO | WO2012167251 | 12/2012 |
| WO | WO2012177443 | 12/2012 |
| WO | WO2013130683 A2 | 9/2013 |
| WO | WO2017114425 | 7/2017 |

OTHER PUBLICATIONS

Wells, 1990, Biochemistry 29:8509-8517.*
Ngo et al., 1994, The Protein Folding Problem and Tertiary Structure Prediction, pp. 492-495.*
Gutniak et al., New England J. Med. 30 326:1316-1322, 1992.*
Clemmensen, et al., "GLP-1/Glucago Coagonism Restores Leptin Responsiveness in Obese Mice Chronically Maintained on an Obesogenic Diet" Diabetes Apr. 2014 vol. 63 pp. 1422-1427.
Day, et al., "A new glucagon and GLP-1 co-agonist eliminates obesity in rodents", Nature Chemical Biology Oct. 2009 vol. 5 No. 10 pp. 749-757.
Russian Office Action cited in 2018127330, dated May 22, 2019.
Korean Office Action cited in 9-5-2019-044175142, dated Jun. 20, 2019.
Australian Office Action cited in 2016383387, dated May 14, 2019.
Clemmensen, "GLP-1/Glucagon Coagonism Restores Leptin Responsiveness in Obese Mice Chronically Maintained on an Obesogenic Diet", 2013 American Diabetes Association.

(Continued)

*Primary Examiner* — Gyan Chandra
(74) *Attorney, Agent, or Firm* — Workman Nydegger

(57) ABSTRACT

The present invention provides a composition comprising a GLP-1 receptor agonist and a glucagon receptor agonist and an application of the composition. More specifically, the present invention provides a pharmaceutical composition comprising a pharmaceutically effective amount of the GLP-1 receptor agonist and the glucagon receptor agonist, wherein the GLP-1 receptor agonist and the glucagon receptor agonist independently form a conjugate with a hydrophilic polymer, or the GLP-1 receptor agonist and the glucagon receptor agonist jointly form a conjugate with the hydrophilic polymer.

6 Claims, 21 Drawing Sheets
Specification includes a Sequence Listing.

(56) References Cited

OTHER PUBLICATIONS

International Search Report cited in PCT Application No. PCT/CN2016/112674 dated Apr. 12, 2017.

Patel "Co-agonist of glucagon and GLP-1 reduces cholesterol and improves insulin sensitivity independent of its effect on appetite and body weigh in diet-induced obese C57 mice", Can. J. Physiol. Pharmacol. 91: 1009-1015 (2013).

T. M. Tan et al.., "Coadministration of Glucagon-Like Peptide-1 During Glucagon Infusion in Humans Results in Increased Energy Expenditure and Amelioration of Hyperglycemia & Site-specific PEGylation of exenatide analogues markedly improved their glucoregulatory activity", Diabetes, vol. 62, Apr. 2013.

Nian Gong, et al., "Site-specific PEGylation of exenatide analogues markedly improved their glucoregulatory activity", British Journal of Pharmacology, vol. 163, No. 2, May 1, 2011.

European Search Report cited in 16881214.7-1112/3406264 PCT/CN2016112674, dated Jun. 18, 2019.

Pocai, et al.,"Glucagon-Like Peptide 1/Glucagon Receptor Dual Agonism Reverses Obesity in Mice" Diabetes, vol. 58, Oct. 2009.

Chinese Office Action issued in 201511017796.2 dated Apr. 23, 2020.

* cited by examiner

SEQUENCE LISTING

```
<160> NUMBER OF SEQ ID NOS: 6

<210> SEQ ID NO 1
<211> LENGTH: 39
<212> TYPE: PRT
<213> ORGANISM: Artificial Sequence
<220> FEATURE:
<223> OTHER INFORMATION: synthetic

<400> SEQUENCE: 1

His Gly Glu Gly Thr Phe Thr Ser Asp Leu Ser Lys Gln Met Glu Glu
1               5                   10                  15
```

Glu Ala Val Arg Leu Phe Ile Glu Trp Leu Lys Asn Gly Gly Pro Ser
            20                  25                  30

Ser Gly Ala Pro Pro Cys
        35

<210> SEQ ID NO 2
<211> LENGTH: 29
<212> TYPE: PRT
<213> ORGANISM: Homo sapiens

<400> SEQUENCE: 2

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 3
<211> LENGTH: 29
<212> TYPE: PRT
<213> ORGANISM: Artificial Sequence
<220> FEATURE:
<223> OTHER INFORMATION: synthetic

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 4
<211> LENGTH: 29
<212> TYPE: PRT
<213> ORGANISM: Artificial Sequence
<220> FEATURE:
<223> OTHER INFORMATION: synthetic

<400> SEQUENCE: 4

His Ser Gln Gly Thr Phe Thr Ser Asp Tyr Ser Lys Tyr Leu Asp Ser
1               5                   10                  15

Arg Arg Ala Gln Asp Phe Val Cys Trp Leu Met Asn Thr
            20                  25

<210> SEQ ID NO 5
<211> LENGTH: 30
<212> TYPE: PRT
<213> ORGANISM: Artificial Sequence
<220> FEATURE:
<223> OTHER INFORMATION: synthetic

<400> SEQUENCE: 5

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Cys
            20                  25                  30

<210> SEQ ID NO 6
<211> LENGTH: 29
<212> TYPE: PRT
<213> ORGANISM: Artificial Sequence
<220> FEATURE:
<223> OTHER INFORMATION: synthetic

<400> SEQUENCE: 6

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25
```

COMPOSITION COMPRISING GLP-1 RECEPTOR AGONIST AND GLUCAGON RECEPTOR AGONIST AND APPLICATION THEREOF

CROSS REFERENCE TO RELATED APPLICATIONS

This application is a 371 Application of International Patent Application No. PCT/CN2016/112674, filed Dec. 28, 2016, which claims the benefit of Chinese Patent Application No. 201511017796.2, filed Dec. 29, 2015 with the State Intellectual Property Office of People's Republic of China and titled with "COMPOSITION COMPRISING GLP-1 RECEPTOR AGONIST AND GLUCAGON RECEPTOR AGONIST AND APPLICATION THEREOF", the disclosures of which are hereby incorporated by reference.

REFERENCE TO A SEQUENCE LISTING SUBMITTED ON COMPUTER

The content of the ASCII text file of the sequence listing named "COMPOSITION COMPRISING GLP-1 RECEPTOR AGONIST AND GLUCAGON RECEPTOR AGONIST AND APPLICATION THEREOF," which was filed in PCT/CN2016/112674 on Dec. 28, 2016, downloaded from the WIPO database, is 3.0 kb in size with a created date of Jun. 7, 2017, and electronically submitted via EFS-Web herewith the application, is incorporated herein by reference in its entirety.

FIELD

The present disclosure relates to the field of medicine, in particular, relates to a composition comprising a GLP-1 receptor agonist and a glucagon receptor agonist and the use for weight loss and/or lipid lowering.

BACKGROUND

In recent years, as the economic development has brought about changes in diet and lifestyle, the proportion of obese people has increased year by year. According to the latest statistics from the World Health Organization, the number of obese and overweight people in the world has surged from 857 million in 1980 to 2.1 billion in 2013, accounting for nearly one third of the global population. In 2014, over 1.9 billion adults aged 18 and over were overweight, of which 600 million were obese. In 2014, 39% of adults aged 18 and over were overweight and 13% were obese. Overweight and obesity, once considered a problem for high-income countries, are now on the rise in low- and middle-income countries. Being overweight and obese increases blood pressure and cholesterol levels in the blood, which are major risk factors for several long-term diseases including diabetes, cardiovascular disease and cancer.

Lifestyle interventions (appropriate exercise and healthy diet) often do not fully control the development of obesity. In this case, drug intervention is considered appropriate and necessary. Orlistat is currently the only OTC diet pill in the world. Over 40 million people worldwide used Orlistat and successfully lost weight. It is currently the best-selling weight loss product. Orlistat is a potent, long-acting, and specific gastrointestinal lipase inhibitor that directly blocks the body's absorption of fat in food, whereby the body fat will decrease when the intake of energy and fat is less than the consumption, so as to achieve the purpose of weight loss. However, Orlistat has several disadvantages, for example, its weight loss effect is not significant for some people, and it needs to be taken with meals every day or after meals, so that patient compliance is poor. Moreover, Orlistat also has safety risks. In May 2010, the U.S. Food and Drug Administration warned of the risk that Orlistat may cause serious liver damage. Therefore, there is a need to develop new weight loss drugs acting through other mechanisms.

Glucagon-like peptide-1 (GLP-1) is a polypeptide hormone secreted by the intestinal L-cells after eating, which can stimulate insulin secretion from pancreatic islet β cells, thereby stabilizing the level of postprandial blood sugar level. Exogenous administration of GLP-1 normalizes blood sugar level levels in patients with type II diabetes. The effect of GLP-1 on lowering blood sugar level is dependent on glucose concentration, thereby greatly reducing the risk of hypoglycemia while regulating blood sugar level. Drugs based on GLP-1, such as Byetta, Victoza, Albiglutide, and Dulaglutide, have been successfully marketed in recent years and are gradually occupying important positions among diabetes drugs.

Clinical application found that GLP-1 drugs have the effect of reducing weight while reducing blood sugar level. The mechanism may be that GLP-1 can act on the gastrointestinal tract to delay gastric emptying and intestinal peristalsis, and GLP-1 can act on the central nervous system to suppress appetite, increase satiety and so on, so as to achieve the purpose of reducing food intake. In 2014, Novo Nordisk's Victoza was even approved for weight loss as an additional indication. However, due to the short half-life of Victoza, patients treated with Victoza need to take one shot every day, increasing the pain of the patients in long-term use.

Glucagon is a peptide with 29 amino acids that correspond to amino acids 53 to 81 of preproglucagon and has the following sequence:
His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr (SEQ ID NO: 2). Oxyntomodulin (OXM) is a peptide with 37 amino acids, which comprises the complete 29 amino acid sequence of glucagon and the carboxy-terminal extension of an octapeptide (amino acids 82 to 89 of preproglucagon). Both Merck and Zeland are developing oxyntomodulin derivatives for use in weight loss and decreasing glucose level. A dual-agonist peptide project for weight loss developed by Merck has entered phase I clinical trial, while zp2929 developed by Zeland's is still in the preclinical phase.

Although using oxyntomodulin for weight loss has an attractive prospect, it still has its shortcomings. For example, the half-life of oxyntomodulin in human plasma is very short (8 to 12 minutes); as a dual-agonist, its activity is poor, and the ability to activate either receptor is much lower than that of the original peptide, making the dose to be administered to a human body needs to reach the level of mg/kg. Moreover, oxyntomodulin exhibits a fixed ratio of agonistic activity for both receptors, which cannot be regulated and may not be the best ratio for exerting its weight loss effect. Therefore, how to optimize drug design to solve these problems has become a top issue for many medical R&D workers.

Exendin-4 is a polypeptide with 39 amino acids isolated from the saliva of the Mexican lizard, which shows 53% homology to GLP-1. Studies have shown that Exendin-4 also binds to GLP-1 receptor and exhibits pharmacologically similar agonistic activity as GLP-1.

Nonalcoholic fatty liver disease (NAFLD) refers to the pathophysiological syndrome that is characterized by excess deposition of fat in the liver cells caused by definitive liver damage factors except alcohol. It is an acquired metabolic stress liver injury and is closely related to insulin resistance and genetic susceptibility. NAFLD includes simple fatty liver (SFL), nonalcoholic steatohepatitis (NASH) and related cirrhosis. With the prevalence of obesity and its associated metabolic syndrome worldwide, nonalcoholic fatty liver disease has now become an important cause of long-term liver disease in Europe, the United States and other developed countries and rich regions in China. In normal adult, the prevalence rate of NAFLD is 10% to 30%, of which 10% to 20% is NASH, and the latter has an incidence of cirrhosis as high as 25% within 10 years. Nonalcoholic fatty liver disease not only can directly lead to compensatory liver cirrhosis, hepatocellular carcinoma and liver graft recurrence, but also can affect the progression of other long-term liver diseases and participate in the pathogenesis of type II diabetes and atherosclerosis. Metabolic syndrome-related malignancies, arteriosclerotic cardiovascular and cerebrovascular diseases, and cirrhosis are important factors affecting the life quality and life expectancy of patients with nonalcoholic fatty liver disease. For above reasons, nonalcoholic fatty liver disease is a new challenge in the field of modern medicine, and in the near future, the impact of nonalcoholic fatty liver disease on human health will continue to increase.

SUMMARY

The inventors surprisingly discovered in the study that simultaneous administration of hydrophilic polymer-modified GLP-1 receptor agonist and hydrophilic polymer-modified glucagon receptor agonist, whether they are linked together or presented separately, achieved much better effect (e.g., weight loss) than using GLP-1 receptor agonist alone. Moreover, while achieving higher activity, it also greatly prolongs the half-life in the body and reduces the frequency of administration. In particular, the technical solution of the present disclosure can also improve the symptoms of fat metabolism disorders in obese animals in addition to reducing body weight, and significantly reduces the amount of triglyceride in serum and liver as well as the amount of serum total cholesterol of the animals after long-term administration, which provides a new possibility for the treatment of nonalcoholic fatty liver.

In one aspect, the present disclosure provides a pharmaceutical composition comprising a pharmaceutically effective amount of a GLP-1 receptor agonist and a glucagon receptor agonist, wherein the GLP-1 receptor agonist and the glucagon receptor agonist independently form a conjugate with a hydrophilic polymer, respectively, or the GLP-1 receptor agonist and the glucagon receptor agonist form a conjugate via a hydrophilic polymer. Optionally, the pharmaceutical composition of the present disclosure further comprises a pharmaceutically acceptable carrier.

In some embodiments, the pharmaceutical composition of the present disclosure can be used for preventing or treating nonalcoholic fatty liver disease, losing weight and/or lowering lipid level. In other embodiments, the pharmaceutical composition of the present disclosure can be used to suppress the appetite in a subject, lower serum total cholesterol content, and/or reduce triglyceride content in liver.

In some embodiments, the GLP-1 receptor agonist and the glucagon receptor agonist in the pharmaceutical composition of the present disclosure are covalently linked via a hydrophilic polymer to form a conjugate.

In some embodiments, the hydrophilic polymer in the pharmaceutical composition of the present disclosure has a molecular weight of 2 kDa to 60 kDa, 5 kDa to 50 kDa, preferably 10 kDa to 40 kDa, more preferably 20 kDa to 40 kDa, particularly 15 kDa to 30 kDa, more particularly 21 kDa to 29 kDa. In particular, the polymer (e.g., PEG) has a molecular weight of about 2 kDa to about 50 kDa, preferably about 3 kDa to about 40 kDa, more preferably about 4 kDa to about 35 kDa, even more preferably about 5 kDa to about 30 kDa, for example, about 5 kDa, about 10 kDa, about 15 kDa, about 20 kDa, 21 kDa, 22 kDa, 23 kDa, 24 kDa, about 25 kDa, 26 kDa, 27 kDa, 28 kDa, 29 kDa, about 30 kDa, about 35 kDa, about 40 kDa and about 45 kDa, or any value between the above molecular weight values.

In some embodiments, the GLP-1 receptor agonist is selected from the group consisting of Exendin-4, Exendin-3 and GLP-1. In particular, the GLP-1 receptor agonist is selected from PB-105 (for example, it has the sequence as shown in SEQ ID NO: 1).

In some embodiments, the glucagon receptor agonist is glucagon. In particular, the glucagon is PB-702 (for example, it has the sequence as shown in SEQ ID NO: 3, wherein the amino group at the side chain of the lysine at the $12^{th}$ position of the sequence is connected with a cysteine group via an amide bond), PB-703 (for example, it has the sequence as shown in SEQ ID NO: 4, wherein glutamine at the $24^{th}$ position of the sequence is substituted with cysteine), PB-740 (for example, it has the sequence as shown in SEQ ID NO: 5, wherein a cysteine residue is added after the $29^{th}$ amino acid) or PB-741 (for example, it has the sequence as shown in SEQ ID NO: 6, wherein the side chain "—CO—NH$_2$" of the glutamine at the $24^{th}$ position is modified to "—CO—NH—CH$_2$CH$_2$—SH").

In some embodiments, the glucagon sequence is modified at one or more positions in reference to the wild-type glucagon sequence. In particular, the modification is the introduction of functional group for coupling to the side chain of lysine, glutamic acid, glutamine, aspartic acid or asparagine (for example, sulfhydryl, azide, maleimide, amino group, alkynyl, vinyl sulfone, halogen or aldehyde group). For example, the modifications include the addition of cysteine to the side chain of lysine at the $12^{th}$ position of SEQ ID NO: 2, the addition of thioglycolic acid to the side chain of lysine at the $12^{th}$ position of SEQ ID NO: 2, the addition of mercaptopropionic acid to the side chain of lysine at the $12^{th}$ position of SEQ ID NO: 2, the addition of mercaptoethyl to the side chain of glutamine at the $24^{th}$ position of SEQ ID NO: 2, the addition of mercaptopropyl to the side chain of glutamine at the $24^{th}$ position of SEQ ID NO: 2 and the addition of mercaptopropionic acid to the side chain of glutamine at the $24^{th}$ position of SEQ ID NO: 2.

Additionally or alternatively, the modification is cysteine addition or substitution, for example, glutamine at the $24^{th}$ position of SEQ ID NO: 2 is substituted with cysteine, the lysine at the $12^{th}$ position of SEQ ID NO: 2 is substituted with cysteine, and/or a cysteine is added after the $29^{th}$ position of SEQ ID NO: 2.

In some embodiments, the hydrophilic polymer is selected from the group consisting of polysaccharide, polypeptide, polyalkylene glycol, polyvinyl pyrrolidone, polyacrylate, polymethacrylate, polyoxazoline, polyvinyl alcohol, polyacrylamide, polymethacrylamide, copolymer of maleic and acrylic acid, polyester, polyacetal, polyorthoester, polycarbonate, polyiminocarbonate, polyamide, vinyl ether maleic anhydride copolymer, styrene maleic anhydride copolymer, and copolymer of the above polymers. In particular, the hydrophilic polymer is selected from polyalkylene glycols such as polyethylene glycol (PEG).

In some embodiments, the molar ratio of the GLP-1 receptor agonist to the glucagon receptor agonist is 1:0.001 to 1:1000, preferably 1:0.01 to 1:100, more preferably 1:0.03 to 1:50, most preferably 1:0.1 to 1:30, particularly 1:0.5 to 1:20, more particularly 1:1 to 1:10, such as 1:0.1, 1:0.2, 1:0.3, 1:0.4, 1:0.5, 1:0.6, 1:0.7, 1:0.8, 1:0.9, 1:1, 1:2, 1:3, 1:4, 1:5, 1:6, 1:7, 1:8, 1:9, 1:10, 1:15, 1:20, 1:25, 1:30 and any value between the above ratios.

In another aspect, the present disclosure provides a pharmaceutical composition comprising a PEGylated GLP-1 receptor agonist and a PEGylated glucagon receptor agonist. In particular, the PEGylated GLP-1 receptor agonist is selected from the group consisting of PB-119, PB-120 and PB-107; the PEGylated glucagon receptor agonist is selected from the group consisting of: PB-707, PB-708, PB-709, PB-713, PB-721 and PB-722.

In another aspect, the present disclosure provides a conjugate comprising a GLP-1 receptor agonist and a glucagon receptor agonist, wherein the GLP-1 receptor agonist and the glucagon receptor agonist form a conjugate via hydrophilic polymer.

In the conjugate of the present disclosure, the GLP-1 receptor agonist and/or the glucagon receptor agonist are conjugated with hydrophilic polymers directly or via a linker, preferably via the sulfhydryl of a cysteine or another amino acid.

In another aspect, the present disclosure provides a conjugate having the general formula $X_1$—$Z_1$—Y—$Z_2$—$X_2$, wherein $X_1$ represents a GLP-1 receptor agonist, $X_2$ represents a glucagon receptor agonist, Y represents a hydrophilic polymer, $Z_1$ represents a first linker, and $Z_2$ represents a second linker. In particular, the present disclosure provides a conjugate having the formula Exendin-4-$Z_1$-PEG-$Z_2$-glucagon, for example, a conjugate having the formula PB105-PEG-PB703 (for example, PB-716, PB-717, PB-718, PB-719, PB-720).

In the present disclosure, the linker, the first linker, and/or the second linker each independently has a group formed by activation of a reactive group (for example, maleimide, halogen, vinyl sulfone, disulfide bond, sulfhydryl, aldehyde, carbonyl, O-substituted hydroxylamine, active ester, alkenyl, alkynyl, azide or other groups with high chemical reactivity). More preferably, the reactive group is selected from the group consisting of maleimide, halogen, vinyl sulfone and disulfide bond.

In the present disclosure, the linker, the first linker, and/or the second linker each independently comprises an activated reactive group (for example, maleimide, halogen, vinyl sulfone, disulfide bond, thiol, aldehyde, carbonyl, O-substituted hydroxylamine, active ester, alkenyl, alkynyl, azide or other groups with high chemical reactivity). More preferably, the reactive group is selected from the group consisting of maleimide, halogen, vinyl sulfone and disulfide bond.

In some embodiments, the hydrophilic polymer is activated for conjugating with the GLP-1 receptor agonist and the glucagon receptor agonist. Preferably, the polymer is a modified polymer having reactive group, for the polymer to conjugate with the GLP-1 receptor agonist and the glucagon receptor agonist via the activation of the reactive group. More preferably, the reactive group is selected from the group consisting of maleimide, halogen, vinyl sulfone, disulfide bond, thiol, aldehyde, carbonyl, O-substituted hydroxylamine, active ester, alkenyl, alkynyl, azide, and other groups with high chemical reactivity.

In another aspect, the present disclosure provides a pharmaceutical composition comprising the following: a combination of PB-721 and PB-119, a combination of PB-722 and PB-119, and a combination of PB-708 and PB-120; or it comprises a component selected from the following: PB-716, PB-717, PB-718, PB-719 and PB-720. Specifically, the structures of PB-119, PB-120, PB-707, PB-708, PB-709, PB-713, PB-716, PB-717, PB-718, PB-719, PB-720, PB-721 and PB-722 are shown in Table 1.

In another aspect, the present disclosure provides a kit comprising the pharmaceutical composition or conjugate according to the present disclosure, and optionally instruction for use.

In another aspect, the present disclosure provides use of the composition or conjugate of the present disclosure for the manufacture of a medicament for preventing or treating nonalcoholic fatty liver disease, losing weight and/or lowering lipid level.

In another aspect, the present disclosure provides use of the composition or conjugate of the present disclosure for the manufacture of a medicament for inhibiting appetite in a subject, lowering serum total cholesterol and/or reducing triglyceride content in the liver.

In another aspect, the present disclosure provides the composition or conjugate as described above for use for preventing or treating nonalcoholic fatty liver disease, weight loss and/or lipid-lowering.

In another aspect, the present disclosure provides the composition or conjugate as described above for use for inhibiting appetite in a subject, lowering serum total cholesterol and/or reducing triglyceride content in the liver.

In another aspect, the present disclosure provides a method for preventing or treating nonalcoholic fatty liver disease, losing weight and/or lowering lipid level, comprising administering the composition or conjugate according to the present disclosure to a subject in need thereof.

In another aspect, the present disclosure provides a method for inhibiting appetite in a subject, lowering serum total cholesterol level and/or reducing triglyceride content in the liver, comprising administering the composition or conjugate according to the present disclosure to a subject in need thereof.

The inventors have also unexpectedly discovered that the composition and conjugate of the present disclosure greatly reduce the frequency of dosing required to maintain the desired effect. In some embodiments, the conjugate of the present disclosure is administered to the subject at a frequency of once at least every 30 days, once at least every 25 days, once at least every 20 days, once at least every 15 days, once at least every 10 days, once at least every 9 days, once at least every 8 days, once at least every 7 days, once at least every 6 days, once at least every 5 days, once at least every 4 days, once at least every 3 days, once at least every 2 days, and once at least every day. In some embodiments, the conjugate of the present disclosure is administered to the subject at a frequency of once at most every 30 days, once at most every 25 days, once at most every 20 days, once at most every 15 days, once at most every 10 days, once at most every 9 Day, once at most every 8 days, once at most every 7 days, once at most every 6 days, once at most every 5 days, once at most every 4 days, once at most every 3 days, once at most every 2 days, and once at most every day.

The composition and conjugate of the present disclosure greatly reduce the frequency of dosing and increase subject compliance.

The composition and conjugate of the present disclosure can be used to prevent weight gain or to promote weight loss. "Preventing" refers to suppressing or reducing weight gain compared to no treatment, and does not necessarily mean a complete stoppage of weight gain. The composition and conjugate of the present disclosure may cause a decrease in food intake and/or an increase in energy expenditure, resulting in a visible effect on body weight. Independent of its effect on body weight, the composition and conjugate of the present disclosure may have a beneficial effect on glucose tolerance and circulating cholesterol levels (for example, reduce circulating LDL levels and increase the HDL/LDL ratio). Thus, the compound of the present disclosure can be used to directly or indirectly treat any condition caused by or characterized by overweight, such as the treatment and/or prevention of obesity, morbid obesity, obesity-related inflammation, obesity-related gallbladder disease or obesity-induced sleep apnea. The composition and conjugate of the present disclosure can be also used to treat metabolic syndrome, insulin resistance, glucose intolerance, type II diabetes, hypertension, atherogenic dyslipidimia, atherosclerosis, arteriosclerosis, coronary heart disease, or stroke. Their role in these disorders can be caused by or related to their effects on body weight, or they can be independent of their effect on body weight.

DETAILED DESCRIPTION

Definition

Figure 1:
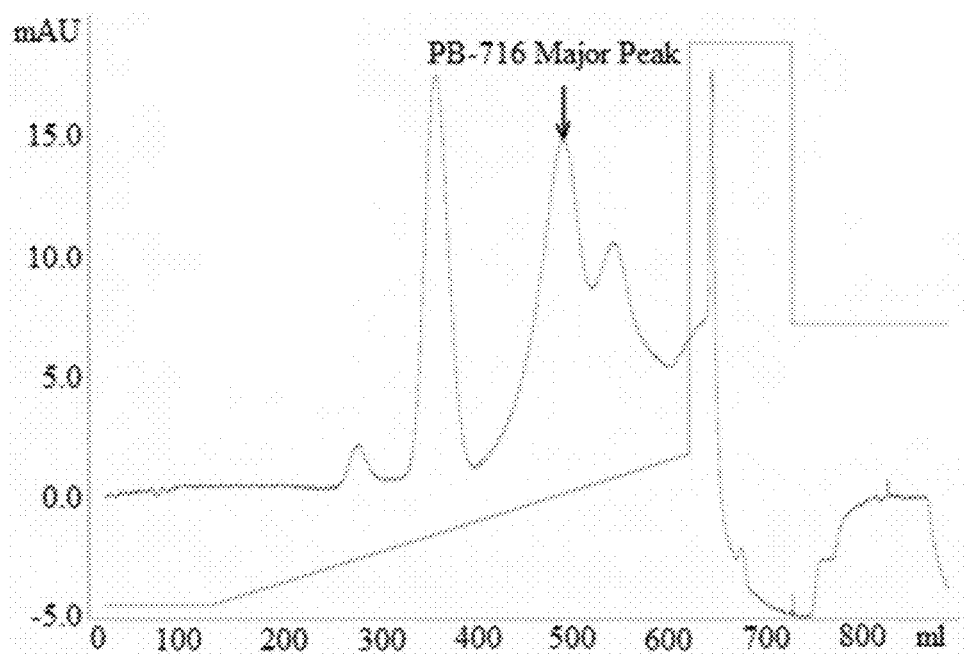
FIG. 1 shows the purification profile of PB-716.

As used herein, the terms "linker," "first linker," "second linker," and the like, refer to group, segment, chemical bond, or any entity that serves to connect a polymer to a biologically active molecule in the present disclosure. In the present disclosure, the linker may contain an activating group (e.g., maleimide, halogen, vinyl sulfone, disulfide bond, sulfhydryl, aldehyde, carbonyl, O-substituted hydroxylamine, active ester, alkenyl, alkynyl, azide, or other groups with high chemical reactivity), for example MAL, ppMAL and the like.

The "polyethylene glycol" described herein has the meaning commonly understood by a person of ordinary skill in the art, and includes both polyethylene glycol (including different structures, for example, linear, branched or bifurcated structure such as star shape) and the terminally modified derivatives thereof, unless otherwise specified. For example, the PEG is methoxy polyethylene glycol (mPEG). Herein, if not specifically stated, the polyethylene glycol (PEG) includes both types in which the terminal group is a hydroxyl group or other groups. The other groups include, but are not limited to, alkoxy, cycloalkoxy, cycloalkyloxy, alkenyl, aryloxy, or aralkyloxy. These PEG types are all known in the art and are commonly used in polypeptide modification. The PEG side chain can be linear, branched, bifurcated or consist of multiple arms, and different polyethylene glycols can have different polymer chain lengths and aggregate structure.

As used herein, "conjugate" refers to a product formed by covalently linking a molecule having biological activity (e.g., GLP-1 receptor agonist and glucagon receptor agonist) with a polyethylene glycol molecule directly or via a linker.

Also, there are many ways to determine the molecular weight of a polymer such as polyethylene glycol. Since the polymer is composed of molecules of different degree of polymerization in a certain distribution range, the average molecular weight is generally used to indicate the molecular weight of the polymer. Specifically, it may be a number-average molecular weight, or a weight-average molecular weight. Although there may be some deviations in the number-average molecular weight and weight-average molecular weight when the degree of polymerization of the polymer differs greatly, these two tend to be equal for the polymer with a narrow range of distribution. With respect to the polymers mentioned herein, such as polyethylene glycol, when referring to its molecular weight, it may be either a weight-average molecular weight or a number-average molecular weight, preferably a number-average molecular weight.

The "GLP-1 receptor agonist" described herein refers to a substance that can activate GLP-1 receptor, for example, wild-type GLP-1 and its variants (such as GLP-1-(7-37) amide and GLP-1-(7-36) amide), wild-type exendin-4 and its variants, and wild-type exendin-3 and its variants. In some embodiments of the present disclosure, the conjugate formed by a GLP-1 receptor agonist and a hydrophilic polymer is long-acting. In other embodiments of the present disclosure, the conjugate formed by a GLP-1 receptor agonist and a glucagon receptor agonist together with a hydrophilic polymer is long-acting.

As used herein, "glucagon receptor agonist" refers to a substance that can activate glucagon receptor, such as wild-type glucagon and variants thereof. For example, the glucagon is PB-702 (for example, it has the sequence as shown in SEQ ID NO: 3, wherein the amino group at the side chain of the lysine at the $12^{th}$ position of the sequence is connected with a cysteine group via an amide bond), PB-703 (for example, it has the sequence as shown in SEQ ID NO: 4, wherein the glutamine at the $24^{th}$ position of the sequence is substituted with a cysteine), PB-740 (for example, it has the sequence as shown in SEQ ID NO: 5, wherein a cysteine residue is added after the $29^{th}$ amino acid) or PB-741 (for example, it has the sequence as shown in SEQ ID NO: 6, wherein the side chain "—CO—$NH_2$" of the glutamine at the $24^{th}$ position is modified to "—CO—NH—$CH_2CH_2$—SH"). In some embodiments, the conjugate of the present disclosure formed by a glucagon receptor agonist and a hydrophilic polymer is long-acting.

"Exendin-4" as used herein refers to a polypeptide found in the saliva of toxic iguanas (J. Biol. Chem, 265, 20259-20262, 1990; J. Biol. Chem, 267, 7402-7405, 1992) and its variants that substantially maintain the function of activating the GLP-1 receptor. Wild-type Exendin-4 is highly homologous (53%) to GLP-1 (7-36), which has a sequence of
His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser (SEQ ID NO: 7).

As used herein, "glucagon" refers to a polypeptide corresponding to amino acids 53 to of preproglucagon (having a sequence shown in SEQ ID NO: 2,
His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr) and its variants that substantially maintain the function of activating the glucagon receptor.

As used herein, the term "long-acting" when used for receptor agonist means that the frequency of administration thereof is no more than once a day, preferably up to several days, for example, 1 day, 2 days, 3 days, 4 days, 5 days, 6 days, 7 days, 8 days, 9 days, 10 days, 15 days, 20 days, 25 days, 30 days, 40 days, 50 days or longer.

Terms such as "comprise", "compose", "contain" and "include" are not meant to be limiting. Also, unless specified otherwise, a word without numeral modification includes the plural form, and "or" means "and/or." Unless defined otherwise herein, all technical and scientific terms used herein have the same meaning as commonly understood by one of ordinary skill in the art.

As used herein, "variant" and "functional variant" are used interchangeably and refer to a modified or altered biological molecule, preferably the variant still retains its biological activity. For example, a "variant" of a polypeptide refers to polypeptides that differ in amino acid sequence by one or more substitutions, deletions, insertions, fusions, truncations, or any combination thereof. Variant polypeptides can be fully functional or may lack one or more activities. A fully functional variant may contain, for example, only conservative changes or changes in non-critical residues or non-critical regions. Functional variant may also contain substitution of similar amino acids, resulting in unchanged function or insignificant functional change.

Unless otherwise defined, all technical and scientific terms used herein have the same meaning as commonly understood by one of ordinary skill in the art. For the definition and terminology in the art, a person skilled in the art can refer to Current Protocols in Molecular Biology (Ausubel). Abbreviations for amino acid residues are standard 3-letter and/or 1-letter codes used in the art to represent one of the 20 commonly used L-amino acids.

As used herein, the term "pharmaceutical composition" means a combination of at least one drug and optionally a pharmaceutically acceptable carrier or excipient that are combined together to achieve a particular purpose. In some embodiments, the pharmaceutical composition include combinations that are separated in time and/or space as long as they can act together to achieve the objective of the present disclosure. For example, the ingredients contained in the pharmaceutical composition (e.g., the conjugate of the present disclosure) may be administered to the subject as a whole, or applied separately to the subject. When the ingredients contained in the pharmaceutical composition are separately administered to a subject, the ingredients may be administered to the subject simultaneously or sequentially. Preferably, the pharmaceutically acceptable carrier is water, buffer, isotonic saline solution such as PBS (phosphate buffer), glucose, mannitol, dextrose, lactose, starch, magnesium stearate, cellulose, magnesium carbonate, 0.3% glycerol, hyaluronic acid, ethanol, or polyalkylene glycol such as polypropylene glycol, triglyceride, and the like. The type of pharmaceutically acceptable carrier depends on whether the composition of the invention is formulated for oral, nasal, intradermal, subcutaneous, intramuscular or intravenous administration. The composition according to the invention may comprise wetting agent, emulsifier or buffer substance as additive.

The pharmaceutical composition according to the present disclosure may be administered by any suitable route, for example, orally, nasally, intracutaneously, subcutaneously, intramuscularly or intravenously.

As used herein, "pharmaceutically effective amount" and "effective amount" refer to a dose sufficient to show the benefit to the subject to which it is administered. The actual administered amount, as well as the rate and timing of administration, will depend on the subject's own condition and severity. The prescription of the treatment (such as the determination of the dose, etc.) is ultimately the responsibility of the general practitioner and other doctors, who is counted on to make a decision, usually considering the disease to be treated, the condition of the individual patient, the delivery site, the method of administration, and for other factors known to the doctor.

As used herein, the term "subject" refers to mammal, such as human, but can also be other animals, such as wild animals (e.g., heron, stork, cranes, etc.), livestock (e.g., duck, geese, etc.), or experimental animals (e.g., orangutan, monkey, rat, mouse, rabbit, guinea pig, groundhog, ground squirrel, etc.).

Although the numerical ranges and parameters set forth in the broad scope of the present disclosure encompass approximations, the numerical values set forth in the specific examples are reported as precisely as possible. However, any numerical value inherently necessarily contains a certain error, which is caused by the standard deviation existing in their respective measurements. In addition, all ranges disclosed herein should be understood to encompass any and all sub-ranges contained therein. For example, the recited range of "1 to 10" should be considered to include any and all sub-ranges between the minimum 1 and the maximum 10, inclusive, that is, all sub-ranges starting with a minimum of 1 or more, such as 1 to 6.1, and sub-ranges ending at a maximum of 10 or less, such as 5.5 to 10. In addition, any reference to "incorporated herein" is to be construed as being incorporated by reference in its entirety.

It should be further noted that, as used in this specification, the singular form includes plural form thereof, unless clearly limited to one pointed object. The term "or" may be used interchangeably with the term "and/or" unless the context clearly dictates otherwise.

The following examples are provided to demonstrate and further explain some preferred embodiments and aspects of the present disclosure and should not be construed as limiting the scope thereof.

TABLE 1

Bioactive molecules involved in the present disclosure

| Name | Structure | SEQ ID No. | Description |
| --- | --- | --- | --- |
| PB-105 | HGEGTFTSDL SKQMEEEAVR LFIEWLKNGG PSSGAPPPC | 1 | Exendin-4 variant |
| PB-701 | HSQGTFTSDY SKYLDSRRAQ DFVQWLMNT | 2 | Wild-type glucagon |
| PB-702 | HSQGTFTSDY SK(-Cys) YLDSRRAQ DFVQWLMNT | 3 | Glucagon Variant (12$^{th}$ position) |
| PB-703 | HSQGTFTSDY SKYLDSRRAQ DFVCWLMNT | 4 | Glucagon Variant (24$^{th}$ position) |
| PB-740 | HSQGTFTSDY SKYLDSRRAQ DFVQWLMNTC | 5 | Glucagon Variant (30$^{th}$ position) |
| PB-741 | HSQGTFTSDY SKYLDSRRAQ DFVQ(-CH$_2$CH$_2$SH)WLMNT | 6 | Glucagon Variant (24$^{th}$ position) |
| PB-119 | mPEG-23 KD-ppMAL-PB-105 | | |
| PB-120 | mPEG-25 KD-ppMAL-PB-105 | | |
| PB-107 | mPEG-30 KD-ppMAL-PB-105 | | |
| PB-707 | mPEG-23 KD-ppMAL-PB-703 | | |
| PB-708 | mPEG-25 KD-ppMAL-PB-703 | | |
| PB-709 | mPEG-30 KD-ppMAL-PB-703 | | |
| PB-713 | mPEG-40 KD-ppMAL-PB-703 | | |
| PB-716 | PB-105-PEG-40 KD-(ppMAL)2--PB-703 | | |
| PB-717 | PB-105-PEG-30 KD-(ppMAL)2--PB-703 | | |
| PB-718 | PB-105-PEG-25 KD-(ppMAL)2--PB-703 | | |
| PB-719 | PB-105-PEG-20 KD-(ppMAL)2--PB-703 | | |
| PB-720 | PB-105-PEG-10 KD-(ppMAL)2--PB-703 | | |
| PB-721 | mPEG-23 KD-ppMAL--PB-740 | | |
| PB-722 | mPEG-23 KD-ppMAL--PB-741 | | |

Note:
underline indicates modification

EXAMPLES

Example 1. Preparation of PB-119 (Conjugate of PB-105 and mPEG-ppMAL-23KD)

10 mg PB-105 (purchased from Kaijie Peptide Co., Ltd., Chengdu, China) and 65 mg mPEG23KD-ppMAL (produced by PEGBIO Co., Ltd., China) were weighted and put into a 50 ml glass container (The molar ratio of PB-105 to PEG is 1:1.2). The mixture was dissolved in 5 ml 0.2M PBS buffer (pH 6.5) and reacted at room temperature (25° C.) for 1 hour under stirring. The pH of the reaction solution was adjusted to 4.0 by using hydrochloric acid to terminate the reaction. The reaction solution was stored at 4° C. for purification and future use.

The reaction solution was diluted 5 times with ultrapure water and the pH of the reaction solution was adjusted to 4.0 by using acetic acid. The reaction solution was loaded to a 10 mL Macrocap SP cation exchange column which had been equalized by 3-4 column volumes of buffer A (20 mM HAc—NaAc, pH 4.0). After loading, buffer A (20 mM HAc—NaAc, pH 4.0) was used to wash away excess PEG and 10 column volumes of elution buffer B (20 mM HAc—NaAc, pH4.0+1M NaCl) was used for gradient elution until 30%. Elution peaks were collected in equal volumes and each collected fraction was analyzed by HPLC. The fractions with a purity greater than 95% were combined and quantified to provide samples for subsequent efficacy experiments.

Example 2. Preparation of PB-120 (Conjugate of PB-105 and mPEG-ppMAL-25KD)

10 mg PB-105 (purchased from Kaijie Peptide Co., Ltd., Chengdu, China) and 72 mg mPEG25KD-ppMAL (produced by PEGBIO Co., Ltd., China) were weighted and put into a 50 ml glass container (The molar ratio of PB-105 to PEG is 1:1.2). The mixture was dissolved in 5 ml 0.2M PBS buffer (pH 6.5) and reacted at room temperature (25° C.) for 1 hour under stirring. The pH of the reaction solution was adjusted to 4.0 by using hydrochloric acid to terminate the reaction. The reaction solution was stored at 4° C. for purification and future use.

The reaction solution was diluted 5 times with ultrapure water and the pH of the reaction solution was adjusted to 4.0 by using acetic acid loaded to a 10 mL Macrocap SP cation exchange column which had been equalized by 3-4 column volumes of buffer A (20 mM HAc—NaAc, pH 4.0). After loading, buffer A (20 mM HAc—NaAc, pH 4.0) was used to wash away excess PEG and 10 column volumes of elution buffer B (20 mM HAc—NaAc, pH4.0+1M NaCl) was used for gradient elution until 30%. Elution peaks were collected in equal volumes and each collected fraction was analyzed by HPLC. The fractions with a purity greater than 95% were combined and quantified to provide samples for subsequent efficacy experiments.

Example 3. Preparation of PB-107 (Conjugate of PB-105 and mPEG-ppMAL-30KD)

10 mg PB-105 (purchased from Kaijie Peptide Co., Ltd., Chengdu, China) and 86 mg mPEG30KD-ppMAL (produced by PEGBIO Co., Ltd., China) were weighted and put into a 50 ml glass container (The molar ratio of PB-105 to PEG is 1:1.2). The mixture was dissolved in 5 ml 0.2M PBS buffer (pH6.5) and reacted at room temperature (25° C.) for 1 hour under stirring. The pH of the reaction solution was adjusted to 4.0 by using hydrochloric acid to terminate the reaction. The reaction solution was stored at 4° C. for purification and future use.

The reaction solution was diluted 5 times with ultrapure water and the pH of the reaction solution was adjusted to 4.0 by using acetic acid. The reaction solution was loaded to a 10 mL Macrocap SP cation exchange column which had been equalized by 3-4 column volumes of buffer A (20 mM HAc—NaAc, pH 4.0). After loading, buffer A (20 mM HAc—NaAc, pH 4.0) was used to wash away excess PEG and 10 column volumes of elution buffer B (20 mM HAc—NaAc, pH4.0+1M NaCl) was used for gradient elution until 30%. Elution peaks were collected in equal volumes and each collected fraction was analyzed by HPLC. The fractions with a purity greater than 95% were combined and quantified to provide samples for subsequent efficacy experiments.

Example 4. Preparation of PB-707 (Conjugate of PB-703 and mPEG-ppMAL-23KD)

10 mg PB-703 (purchased from Kaijie Peptide Co., Ltd., Chengdu, China) and 100 mg mPEG-ppMAL-23KD (produced by PEGBIO Co., Ltd., China) were weighted and put into a 50 ml glass container (The molar ratio of PB-703 to PEG is 1:1.5). The mixture was dissolved in 5 ml 0.2M PBS buffer (pH 6.5) and reacted at room temperature (25° C.) for 1 hour under stirring. The pH of the reaction solution was adjusted to 4.0 by using hydrochloric acid to terminate the reaction. The reaction solution was stored at 4° C. for purification and future use.

The reaction solution was diluted 5 times with ultrapure water and the pH of the reaction solution was adjusted to 4.0 by using acetic acid. The reaction solution was loaded to a 10 mL Macrocap SP cation exchange column which had been equalized by 3-4 column volumes of buffer A (20 mM HAc—NaAc, pH 4.0). After loading, buffer A (20 mM HAc—NaAc, pH 4.0) was used to wash away excess PEG and 15 column volumes of elution buffer B (20 mM HAc—NaAc, pH4.0+1M NaCl) was used for gradient elution until 30%. Elution peaks were collected in equal volumes and each collected fraction was analyzed by HPLC. The fractions with a purity greater than 95% were combined and quantified to provide samples for subsequent efficacy experiments.

Example 5. Preparation of PB-708 (Conjugate of PB-703 and mPEG-ppMAL-25KD)

10 mg PB-703 (purchased from Kaijie Peptide Co., Ltd., Chengdu, China) and 110 mg mPEG-ppMAL-25KD (produced by PEGBIO Co., Ltd., China) were weighted and put into a 50 ml glass container (The molar ratio of PB-703 to PEG is 1:1.5). The mixture was dissolved in 5 ml 0.2M PBS buffer (pH 6.5) and reacted at room temperature (25° C.) for 1 hour under stirring. The pH of the reaction solution was adjusted to 4.0 by using hydrochloric acid to terminate the reaction. The reaction solution was stored at 4° C. for purification and future use.

The reaction solution was diluted 5 times with ultrapure water and the pH of the reaction solution was adjusted to 4.0 by using acetic acid. The reaction solution was loaded to a 10 mL Macrocap SP cation exchange column which had been equalized by 3-4 column volumes of buffer A (20 mM HAc—NaAc, pH 4.0). After loading, buffer A (20 mM HAc—NaAc, pH 4.0) was used to wash away excess PEG and 15 column volumes of elution buffer B (20 mM HAc—NaAc, pH4.0+1M NaCl) was used for gradient elution until 30%. Elution peaks were collected in equal volumes and each collected fraction was analyzed by HPLC. The fractions with a purity greater than 95% were combined and quantified to provide samples for subsequent efficacy experiments.

Example 6. Preparation of PB-709 (Conjugate of PB-703 and mPEG-ppMAL-30KD)

10 mg PB-703 (purchased from Kaijie Peptide Co., Ltd., Chengdu, China) and 130 mg mPEG-ppMAL-30KD (produced by PEGBIO Co., Ltd., China) were weighted and put into a 50 ml glass container (The molar ratio of PB-703 to PEG is 1:1.5). The mixture was dissolved in 5 ml 0.2M PBS buffer (pH 6.5) and reacted at room temperature (25° C.) for 1 hour under stirring. The pH of the reaction solution was adjusted to 4.0 by using hydrochloric acid to terminate the reaction. The reaction solution was stored at 4° C. for purification and future use.

The reaction solution was diluted 5 times with ultrapure water and the pH of the reaction solution was adjusted to 4.0 by using acetic acid. The reaction solution was loaded to a 10 mL Macrocap SP cation exchange column which had been equalized by 3-4 column volumes of buffer A (20 mM HAc—NaAc, pH 4.0). After loading, buffer A (20 mM HAc—NaAc, pH 4.0) was used to wash away excess PEG and 15 column volumes of elution buffer B (20 mM HAc—NaAc, pH4.0+1M NaCl) was used for gradient elution until 30%. Elution peaks were collected in equal volumes and each collected fraction was analyzed by HPLC. The fractions with a purity greater than 95% were combined and quantified to provide samples for subsequent efficacy experiments.

Example 7. Preparation of PB-713 (Conjugate of PB-703 and mPEG-ppMAL-40KD)

10 mg PB-703 (purchased from Kaijie Peptide Co., Ltd., Chengdu, China) and 175 mg mPEG-ppMAL-40KD (produced by PEGBIO Co., Ltd., China) were weighted and put into a 50 ml glass container (The molar ratio of PB-703 to PEG is 1:1.5). The mixture was dissolved in 5 ml 0.2M PBS buffer (pH 6.5) and reacted at room temperature (25° C.) for 1 hour under stirring. The pH of the reaction solution was adjusted to 4.0 by using hydrochloric acid to terminate the reaction. The reaction solution was stored at 4° C. for purification and future use.

The reaction solution was diluted 5 times with ultrapure water and the pH of the reaction solution was adjusted to 4.0 by using acetic acid. The reaction solution was loaded to a 10 mL Macrocap SP cation exchange column which had been equalized by 3-4 column volumes of buffer A (20 mM HAc—NaAc, pH 4.0). After loading, buffer A (20 mM HAc—NaAc, pH 4.0) was used to wash away excess PEG and 15 column volumes of elution buffer B (20 mM HAc—NaAc, pH4.0+1M NaCl) was used for gradient elution until 30%. Elution peaks were collected in equal volumes and each collected fraction was analyzed by HPLC. The fractions with a purity greater than 95% were combined and quantified to provide samples for subsequent efficacy experiments.

Example 8. Preparation of PB-721 (Conjugate of PB-740 and mPEG-ppMAL-23KD)

10 mg PB-740 (purchased from Chinese Peptide Co., Ltd., China) and 96 mg mPEG-ppMAL-23KD (produced by PEGBIO Co., Ltd., China) were weighted and put into a 50 ml glass container (The molar ratio of PB-740 to PEG is 1:1.5). The mixture was dissolved in 5 ml 0.2M PBS buffer (pH 6.5) and reacted at room temperature (25° C.) for 1 hour under stirring. The pH of the reaction solution was adjusted to 4.0 by using hydrochloric acid to terminate the reaction. The reaction solution was stored at 4° C. for purification and future use.

The reaction solution was diluted 5 times with ultrapure water and the pH of the reaction solution was adjusted to 4.0 by using acetic acid. The reaction solution was loaded to a 10 mL Macrocap SP cation exchange column which had been equalized by 3-4 column volumes of buffer A (20 mM HAc—NaAc, pH 4.0). After loading, buffer A (20 mM HAc—NaAc, pH 4.0) was used to wash away excess PEG and 15 column volumes of elution buffer B (20 mM HAc—NaAc, pH4.0+1M NaCl) was used for gradient elution until 30%. Elution peaks were collected in equal volumes and each collected fraction was analyzed by HPLC. The fractions with a purity greater than 95% were combined and quantified to provide samples for subsequent efficacy experiments.

Example 9. Preparation of PB-722 (Conjugate of PB-741 and mPEG-ppMAL-23KD)

10 mg PB-741 (purchased from Chinese Peptide Co., Ltd., China) and 97 mg mPEG-ppMAL-23KD (produced by PEGBIO Co., Ltd., China) were weighted and put into a 100 ml glass container (The molar ratio of PB-741 to PEG is 1:1.5). The mixture was dissolved in 5 ml 0.2M PBS buffer (pH 6.5) and reacted at room temperature (25° C.) for 1 hour under stirring. The pH of the reaction solution was adjusted to 4.0 by using hydrochloric acid to terminate the reaction. The reaction solution was stored at 4° C. for purification and future use.

The reaction solution was diluted 5 times with ultrapure water and the pH of the reaction solution was adjusted to 4.0 by using acetic acid. The reaction solution was loaded to a 10 mL Macrocap SP cation exchange column which had been equalized by 3-4 column volumes of buffer A (20 mM HAc—NaAc, pH 4.0). After loading, buffer A (20 mM HAc—NaAc, pH 4.0) was used to wash away excess PEG and 15 column volumes of elution buffer B (20 mM HAc—NaAc, pH4.0+1M NaCl) was used for gradient elution until 300%. Elution peaks were collected in equal volumes and each collected fraction was analyzed by HPLC. The fractions with a purity greater than 95% were combined and quantified to provide samples for subsequent efficacy experiments.

Example 10. Preparation of PB-716 (Conjugate of PB-703, PB-105 and PEG-(ppMAL)2-40KD)

20 mg PB-105 (purchased from Kaijie Peptide Co., Ltd., Chengdu, China), 21 mg PB-703 (purchased from Kaijie Peptide Co., Ltd., Chengdu, China) and 158.6 mg PEG-(ppMAL)2-40KD (produced by PEGBIO Co., Ltd., China) were weighted and put into a 50 ml glass container (The molar ratio of PEG, PB-105 and PB-703 is 1:1.2:1.5). The mixture was dissolved in 10 ml 0.2M PBS buffer (pH 6.5) and reacted at room temperature (25° C.) for 1 hour under stirring. The pH of the reaction solution was adjusted to 4.0 by using hydrochloric acid to terminate the reaction. The reaction solution was stored at 4° C. for purification and future use.

The reaction solution was diluted 5 times with ultrapure water and the pH of the reaction solution was adjusted to 4.0 by using acetic acid. The reaction solution was loaded to a 20 mL Macrocap SP cation exchange column which had been equalized by 3-4 column volumes of buffer A (20 mM HAc—NaAc, pH 4.0). After loading, 3-4 column volumes of buffer A (20 mM HAc—NaAc, pH 4.0) was used to equalize and 30 column volumes of elution buffer B (20 mM HAc—NaAc, pH4.0+1M NaCl) was used for gradient elution until 40%. Elution peaks were collected in equal volumes and each collected fraction was analyzed by HPLC. The fractions with a purity greater than 95% were combined and quantified to provide samples for subsequent efficacy experiments. FIG. 1 shows the purification profile of PB-716.

Example 11. Preparation of PB-717 (Conjugate of PB-703, PB-105 and PEG-(ppMAL)2-30KD)

20 mg PB-105 (purchased from Kaijie Peptide Co., Ltd., Chengdu, China), 21 mg PB-703 (purchased from Kaijie Peptide Co., Ltd., Chengdu, China) and 119 mg PEG-(ppMAL)2-30KD (produced by PEGBIO Co., Ltd., China) were weighted and put into a 100 ml glass container (The molar ratio of PEG, PB-105 and PB-703 is 1:1.2:1.5). The mixture was dissolved in 10 ml 0.2M PBS buffer (pH 6.5) and reacted at room temperature (25° C.) for 1 hour under stirring. The pH of the reaction solution was adjusted to 4.0 by using hydrochloric acid to terminate the reaction. The reaction solution was stored at 4° C. for purification and future use.

Figure 2:
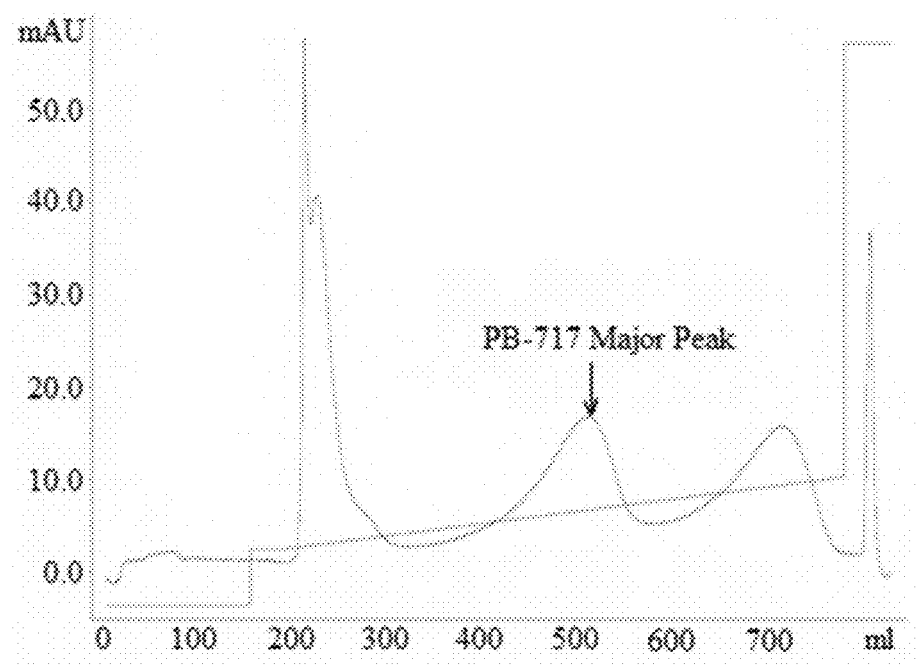
FIG. 2 shows the purification profile of PB-717.

The reaction solution was diluted 5 times with ultrapure water and the pH of the reaction solution was adjusted to 4.0 by using acetic acid. The reaction solution was loaded to 20 mL Macrocap SP cation exchange column which had been equalized by 3-4 column volumes of buffer A (20 mM HAc—NaAc, pH 4.0). After loading, 3-4 column volumes of buffer A (20 mM HAc—NaAc, pH 4.0) was used to equalize and 30 column volumes of elution buffer B (20 mM HAc—NaAc, pH4.0+1M NaCl) was used for gradient elution until 40%. The elution peaks were collected at the same volume. Elution peaks were collected in equal volumes and each collected fraction was analyzed by HPLC. The fractions with a purity greater than 95% were combined and quantified to provide samples for subsequent efficacy experiments. FIG. 2 shows the purification profile of PB-717.

Example 12. Preparation of PB-718 (Conjugate of PB-703, PB-105 and PEG-(ppMAL)2-25KD)

20 mg PB-105 (purchased from Kaijie Peptide Co., Ltd., Chengdu, China), 21 mg PB-703 (purchased from Kaijie Peptide Co., Ltd., Chengdu, China) and 99 mg PEG-(ppMAL)2-25KD (produced by PEGBIO Co., Ltd., China) were weighted and put into a 100 ml glass container (The molar ratio of PEG, PB-105 and PB-703 is 1:1.2:1.5). The mixture was dissolved in 10 ml 0.2M PBS buffer (pH 6.5) and reacted at room temperature (25° C.) for 1 hour under stirring. The pH of the reaction solution was adjusted to 4.0 by using hydrochloric acid to terminate the reaction. The reaction solution was stored at 4° C. for purification and future use.

Figure 3:
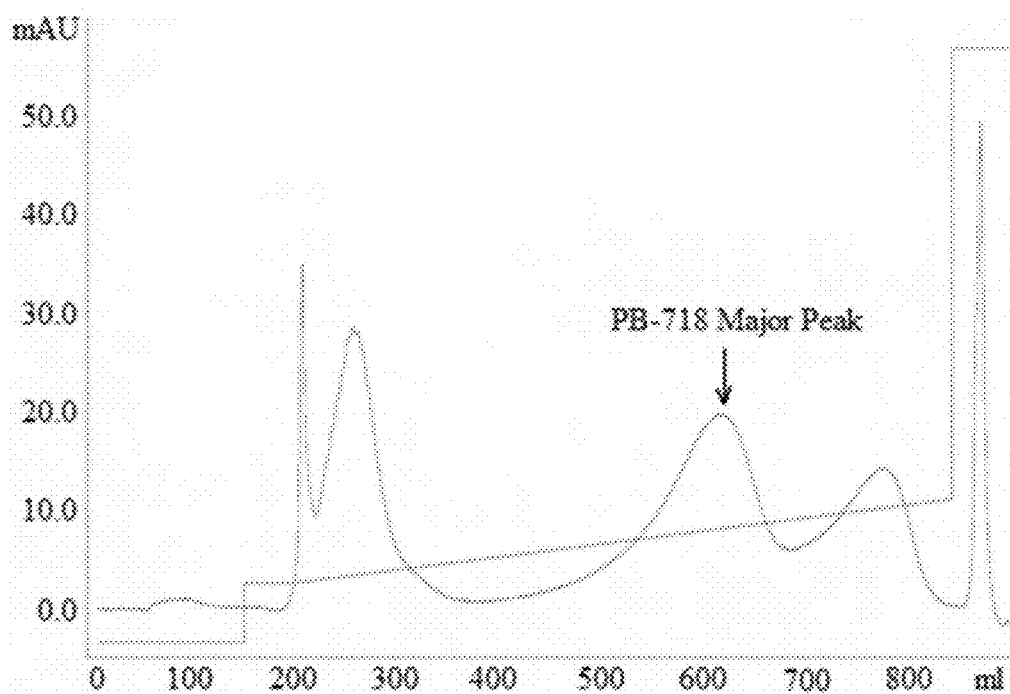
FIG. 3 shows the purification profile of PB-718.

The reaction solution was diluted 5 times with ultrapure water and the pH of the reaction solution was adjusted to 4.0 by using acetic acid. The reaction solution was loaded to a 20 mL Macrocap SP cation exchange column which had been equalized by 3-4 column volumes of buffer A (20 mM HAc—NaAc, pH 4.0). After loading, 3-4 column volumes of buffer A (20 mM HAc—NaAc, pH 4.0) was used to equalize and 30 column volumes of elution buffer B (20 mM HAc—NaAc, pH4.0+1M NaCl) was used for gradient elution until 40%. The elution peaks were collected at the same volume. Elution peaks were collected in equal volumes and each collected fraction was analyzed by HPLC. The fractions with a purity greater than 95% were combined and quantified to provide samples for subsequent efficacy experiments. FIG. 3 shows the purification profile of PB-718.

Example 13. Preparation of PB-719 (Conjugate of PB-703, PB-105 and PEG-(ppMAL)2-20KD)

20 mg PB-105 (purchased from Kaijie Peptide Co., Ltd., Chengdu, China), 21 mg PB-703 (purchased from Kaijie Peptide Co., Ltd., Chengdu, China) and 79.3 mg PEG-(ppMAL)2-20KD (produced by PEGBIO Co., Ltd., China) were weighted and put into a 100 ml glass container (The molar ratio of PEG, PB-105, PB-703 is 1:1.2:1.5). The mixture was dissolved in 10 ml 0.2M PBS buffer (pH6.5) and reacted at room temperature (25° C.) for 1 hour under stirring. The pH of the reaction solution was adjusted to 4.0 by using hydrochloric acid to terminate the reaction. The reaction solution was stored at 4° C. for purification and future use.

Figure 4:
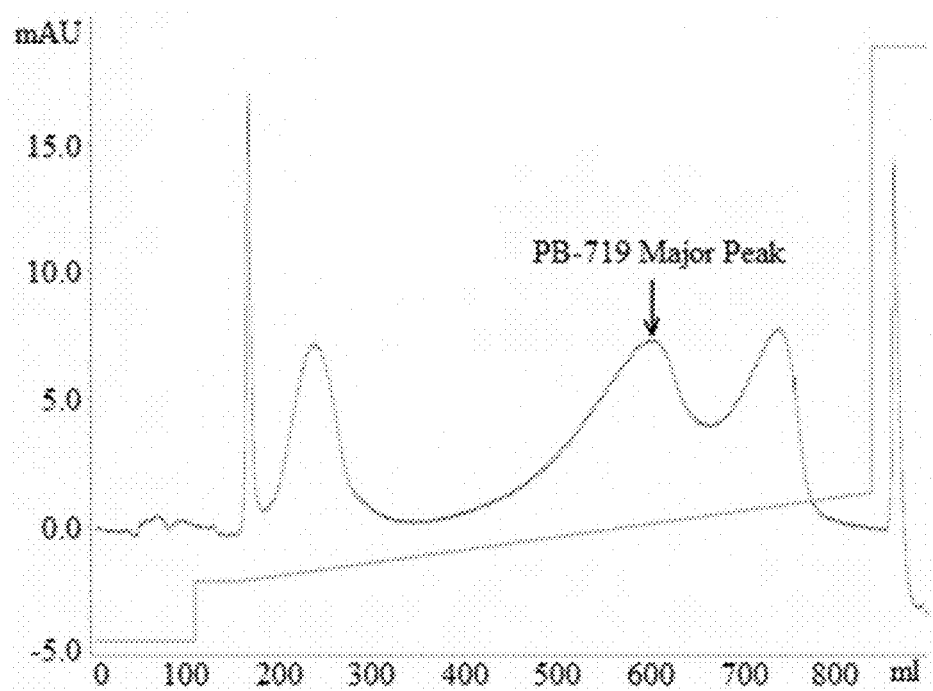
FIG. 4 shows the purification profile of PB-719.

The reaction solution was diluted 5 times with ultrapure water and the pH of the reaction solution was adjusted to 4.0 by using acetic acid. The reaction solution was loaded to a 20 mL Macrocap SP cation exchange column which had been equalized by 3-4 column volumes of buffer A (20 mM HAc—NaAc, pH 4.0). After loading, 3-4 column volumes of buffer A (20 mM HAc—NaAc, pH 4.0) was used to equalize and 30 column volumes of elution buffer B (20 mM HAc—NaAc, pH4.0+1M NaCl) was used for gradient elution until 40%. Elution peaks were collected in equal volumes and each collected fraction was analyzed by HPLC. The fractions with a purity greater than 95% were combined and quantified to provide samples for subsequent efficacy experiments. FIG. 4 shows the purification profile of PB-719.

Example 14. Preparation of PB-720 (Conjugate of PB-703, PB-105 and PEG-(ppMAL)2-10KD)

20 mg PB-105 (purchased from Kaijie Peptide Co., Ltd., Chengdu, China), 21 mg PB-703 (purchased from Kaijie Peptide Co., Ltd., Chengdu, China) and 39.7 mg PEG-(ppMAL)2-10KD (produced by PEGBIO Co., Ltd., China) were weighted and put into a 100 ml glass container (The molar ratio of PEG, PB-105 and PB-703 is 1:1.2:1.5). The mixture was dissolved in 10 ml 0.2M PBS buffer (pH6.5) and reacted at room temperature (25° C.) for 1 hour under stirring. The pH of the reaction solution was adjusted to 4.0 by using hydrochloric acid to terminate the reaction. The reaction solution was stored at 4° C. for purification and future use.

Figure 5:
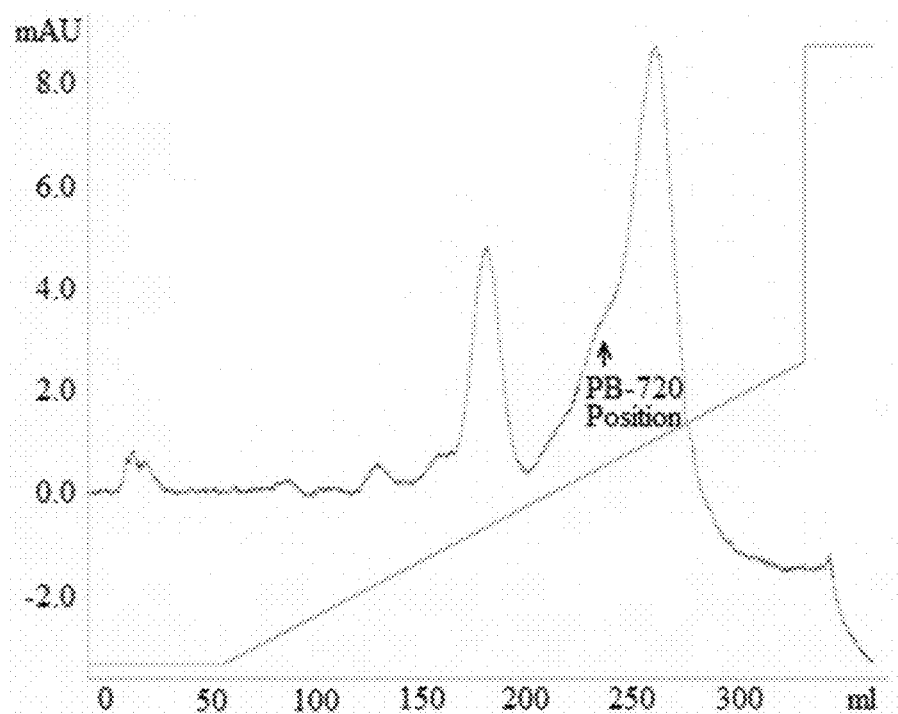
FIG. 5 shows the purification profile of PB-720.

The reaction solution was diluted 5 times with ultrapure water and the pH of the reaction solution was adjusted to 4.0 by using acetic acid. The reaction solution was loaded to a 20 mL Macrocap SP cation exchange column which had been equalized by 3-4 column volumes of buffer A (20 mM HAc—NaAc, pH 4.0). 30 column volumes of elution buffer B (20 mM HAc—NaAc, pH4.0+1M NaCl) was used for gradient elution until 40%. Elution peaks were collected in equal volumes and each collected fraction was analyzed by HPLC. The fractions with a purity greater than 95% were combined and quantified to provide samples for subsequent efficacy experiments. FIG. 5 shows the purification profile of PB-720.

Example 15. In Vitro EC50 of Pegylated Glucagon

HEK293 cells stably expressing the glucagon receptor (HD Biosciences Co., Ltd., Shanghai, China) were cultured in DMEM medium (Hyclone) supplemented with 10% FBS (Hyclone) in an incubator at 37° C. with 10% $CO_2$. The cells were digested with trypsin (Hyclone), seeded in 96-well plate at a density of $5 \times 10^4$ cells/100 µl and incubated for 16-24 hours. Then, the original culture medium was discarded and substituted with serum-free DMEM medium, and incubation was continued for 4 hours. Wild-type glucagon, glucagon variants, and pegylated glucagon were added (final concentrations were 100 nmol/L, 30 nmol/L, 10 nmol/

L, 3 nmol/L, 1 nmol/L, 0.3 nmol/L, 0.1 nmol/L, 0.01 nmol/L, respectively) and incubated with cells for 20 min. The medium with glucagons in different forms was discarded and cell lysis buffer (included in cAMP enzyme-linked immunosorbent assay kit, R&D Systems) was added. The plate was placed in a −80° C. freezer and freeze-thawed twice to lyse the cells. The supernatants were collected by cryogenic centrifugation. Following the manufacturer's instruction of the cAMP enzyme-linked immunosorbent assay kit (R&D Systems), the cAMP concentrations in the supernatant of the sample wells were determined by plotting a standard curve. Graphpad Prism software was used to plot the dose-response curves of glucagon and its variants and EC50 of each sample curve was calculated.

Wild-type glucagon, glucagon variants, and pegylated glucagon have been shown to increase cAMP content in HEK293 cells and/or glucagon R cells in a dose-dependent manner at cellular level, and the EC50 values thereof for stimulating the cells to release cAMP were shown in Table 2.

TABLE 2

In Vitro EC50 of Pegylated Glucagon

| Compound | EC50 (nM) |
|---|---|
| Glucagon | 0.84 |
| PB-702 | 2.23 |
| PB-703 | 1.7 |
| PB-707 | 14.9 |
| PB-716 | 6.2 |
| PB-740 | 1.45 |
| PB-741 | 2.25 |
| PB-721 | 6.94 |
| PB-722 | 12.3 |

Example 16. Experiment for Pharmacological Effect of Long-Term Administration of the Conjugate of the Present Disclosure on Weight Loss in DIO Mice Male C57BL/6 mice (Cavens Lab Animal Co., Ltd., Changzhou, China) were fed with high-fat diet (MD12032, 45% kcal, Medicience Co., Ltd., Jiangsu, China) for 9 weeks, of which the body weight was 20% more than the mice fed with common diet (Suzhou Shuangshi Animal Feed Technology Co., Ltd., China), indicating that the model of obesity-induced obesity (DIO) was successfully established. 35 DIO mice were divided into 7 groups based on their body weight and random blood sugar level, with 5 mice per group, which were PB-716 group (383 µg/kg), PB-717 group (383 µg/kg), PB-718 group (383 µg/kg), PB-719 group (383 µg/kg), PB-720 group (383 µg/kg), Victoza group (200 µg/kg) and model control group (physiological saline) (dose in term of peptide content). After the first administration, each group was observed for 96 hours and then dosed a second time. In the subsequent experiments, the Victoza group was dosed once a day and the remaining groups were dosed once every 3 days. The continuous administration experiments was conducted for a total of 14 days. During the experimental period, the body weight and food intake of the mice were measured every day. Random blood sugar level was measured before the start of the experiment and after the complement of the experiment.

Figure 6:
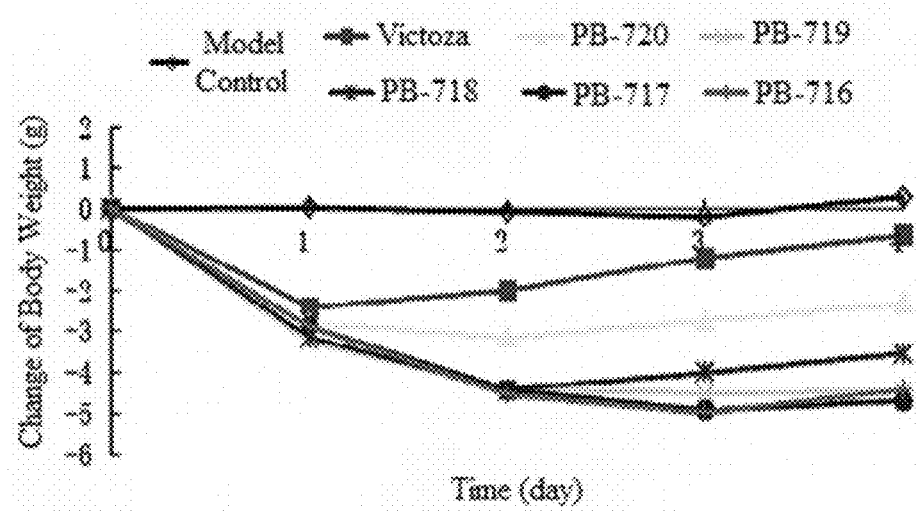
FIG. 6 shows the effect of a single dose of PB-716 series compounds on body weight of DIO mice.

After the first administration, the body weight of each treatment group of animals was significantly lower than that of the control group. The results are shown in FIG. 6. 48-96 hours after administration, body weight of mice in the Victoza group rebounded gradually; by 96 hours, there was no significant difference in body weight between the mice of the Victoza group and the control group. The weight of mice in the PB-720 group remained basically constant during 48-96 hours after administration, with slight rebound. The weight of mice in the PB-716, PB-717, PB-718 and PB-719 groups kept declining until 48 hours after administration and rebounded slightly during 72-96 hours after administration. Compared with the control group, the body weight reduction effect of single administration of PB-716, PB-717, PB-718 and PB-719 can be maintained up to 96 hours after administration, indicating that PEGylation greatly prolongs the acting time of compound in animals.

Figure 7:
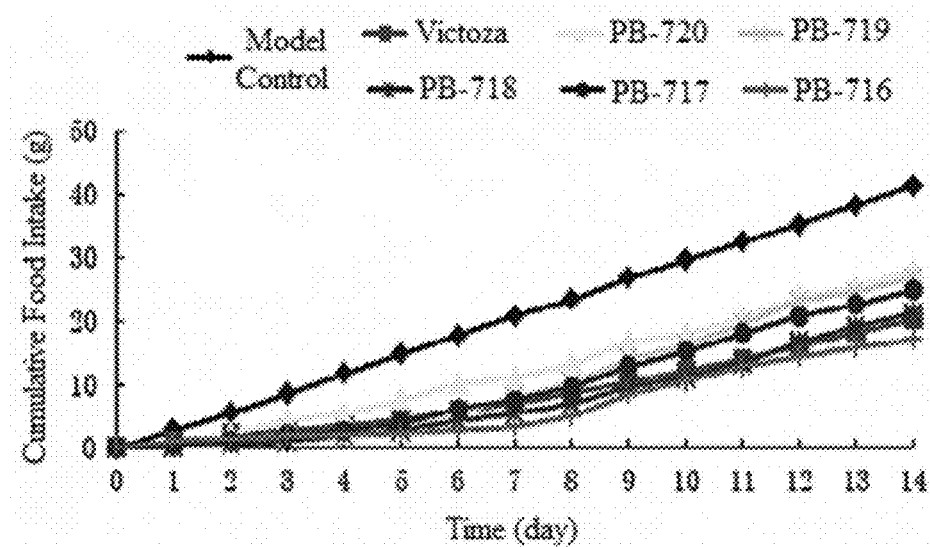
FIG. 7 shows the effect of continuous administration of PB-716 series compounds on cumulative food intake of DIO mice.
Figure 8:
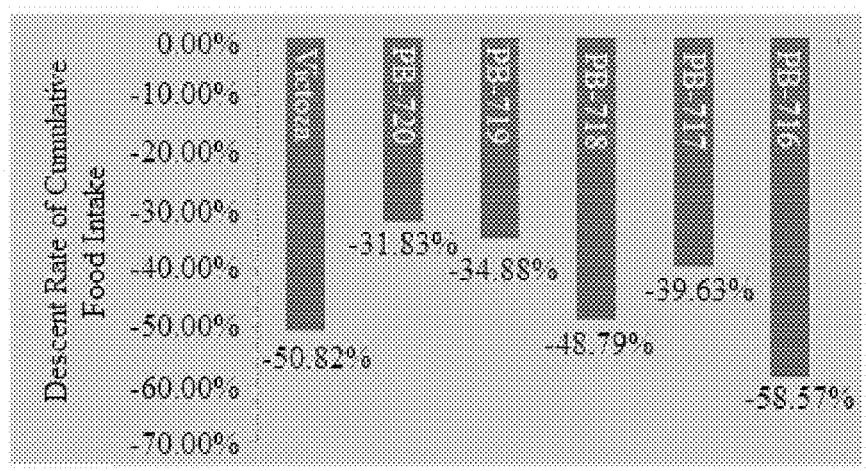
FIG. 8 shows the descent rate of cumulative food intake between the treatment groups and the control model group after administration for 14 consecutive days.

The effect of continuous administration on food intake of DIO mice was shown in FIG. 7. After single administration, the mice were observed for 96 hours and then continuous administration was started, wherein the Victoza group was dosed once a day, and the remaining groups were dosed once every 3 days. Within 14 days after the start of continuous administration, the cumulative food intake of the model control group showed a linear upward trend, while the treatment groups have different degrees of decline in food intake compared with the control group. At the end of the 14-day continuous administration, the cumulative food intake of the PB-716 and Victoza groups reduced the most, up to 58.67% and 50.82%, respectively. The cumulative food intake of PB-720, PB-719, PB-718 and PB-717 groups also decreased by 31.83%, 34.88%, 48.79% and 39.63%, respectively. FIG. 8 showed the descent rate of cumulative food intake of the treatment groups relative to the control model group after administration for 14 consecutive days.

Figure 9:
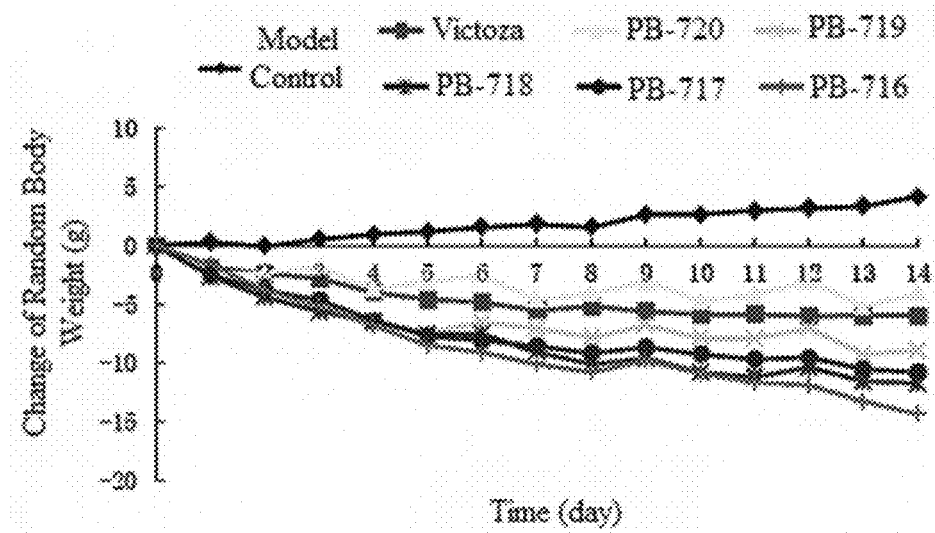
FIG. 9 shows the effect of continuous administration of PB-716 series compounds on body weight of DIO mice.
Figure 10:
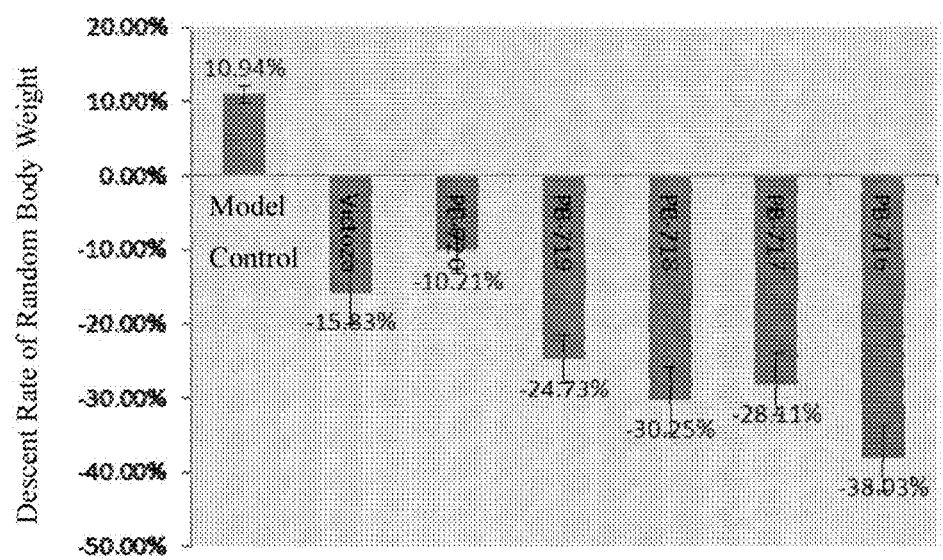
FIG. 10 shows the descent rate of body weight of DIO mice after continuous administration of PB-716 series compounds.

The effect of continuous administration on body weight of DIO mice was shown in FIG. 9 and FIG. 10. At the end of the experiment, the body weight of the model control group increased by 10.24% compared with that before the administration, and the body weight of each treatment group was decreased to different degrees. Among them, the PB-716 group has the most significant decrease, with a weight loss of 38.03% compared with that before the administration, which showed a statistically significant difference from the model control group ($p<0.001$). The weight loss in the other groups was: Victoza group decreased by 15.83% ($p<0.05$) compared with that before the administration; PB-720 group decreased by 10.21% ($p<0.05$); PB-719 group decreased by 24.73% ($p<0.001$); PB-718 group decreased by 30.25% ($p<0.001$); PB-717 group decreased by 28.11% ($p<0.001$), indicating that the long-term administration of PB-716 series compounds have significant inhibition on the body weight of DIO mice.

Figure 11:
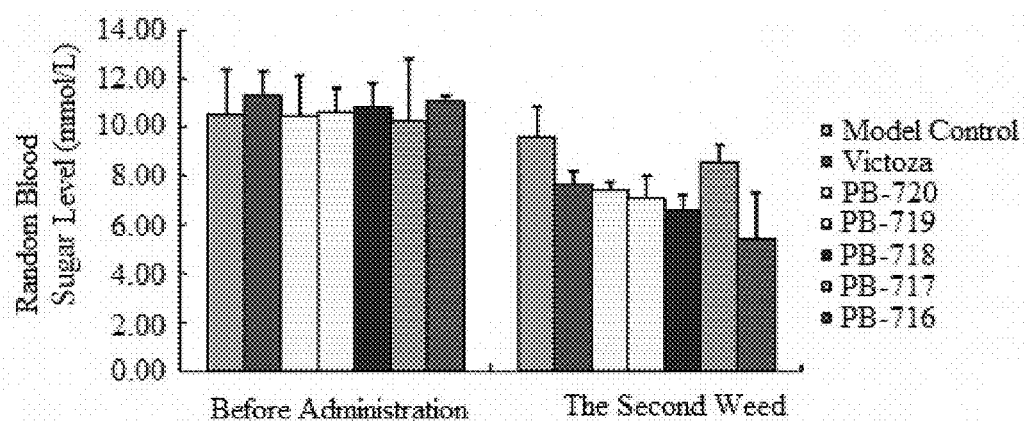
FIG. 11 shows the effect of long-term administration of PB-716 series compounds on random blood sugar level of DIO mice.

The effect of continuous administration on random blood sugar level of DIO mice was shown in FIG. 11. After 9 weeks of high-fat feeding, random blood sugar level of C57BL/6 mice increased to a certain degree. The average random blood sugar level in the normal feeding group was 8.7 mmol/L, while the average random blood sugar level in the high-fat feeding group increased by 33.3%, to 11.6 mmol/L. The random blood sugar level of each treatment group decreased significantly after administration, and the PB-716 group had the largest decrease (51.06% on average) ($P<0.05$). PB-720, PB-719, and PB-718 also decreased by 29.31%, 33.40% and 38.89%, respectively, which showed statistically significant difference ($p<0.05$) from the model control group, indicating that long-term administration of PB-716 series compounds has a hypoglycemic effect on DIO mice.

These results show that the PB-716 series of Exendin-4 and glucagon dual agonist conjugates greatly extend the duration of compound action in animals due to the attachment of PEG molecules. The long-term administration of PB-716 series compounds has obvious inhibitory effect on the food intake of DIO mice, and significantly reduces the body weight of DIO mice, among which PB-716 has the best weight loss effect.

Example 17. Experiment for Pharmacological Effect of Long-Term Administration of the Combination of PB-708 and PB-120 on Weight Loss in DIO Mice Male C57BL/6 mice (Cavens Lab Animal Co., Ltd., Changzhou, China) were fed with high-fat diet (MD12032, 45% kcal, Medicience Co., Ltd., Jiangsu, China) for 12 weeks, of which the body weight was 20% more than the mice fed with common diet (Suzhou Shuangshi Animal Feed Technology Co., Ltd., China), indicating that the model of obesity-induced obesity (DIO) was successfully established. 35 DIO mice were divided into 7 groups based on their body weight and random blood sugar level, with 5 mice per group, which were Victoza group (200 µg/kg), PB-718 high-dose group (383 µg/kg), PB-718 low-dose group (153.2 µg/kg), PB-119 group (210 µg/kg), PEG-OXM (conjugate of natural dual agonist for GLP-1 receptor and glucagon receptor Oxyntomodulin and 23KD PEG) group (222.5 µg/kg), combinational administration group (172.9 µg/kg PB-708+210 µg/kg PB-120) and model control group (physiological saline) (dose in term of peptide content). The Victoza group was dosed once a day and the remaining groups were dosed once every 2 days. The continuous administration experiment was conducted for a total of 14 days. During the experimental period, the body weight and food intake of the mice were measured every day. Random blood sugar level was measured before the start of the experiment and after the complement of the experiment.

Figure 12:
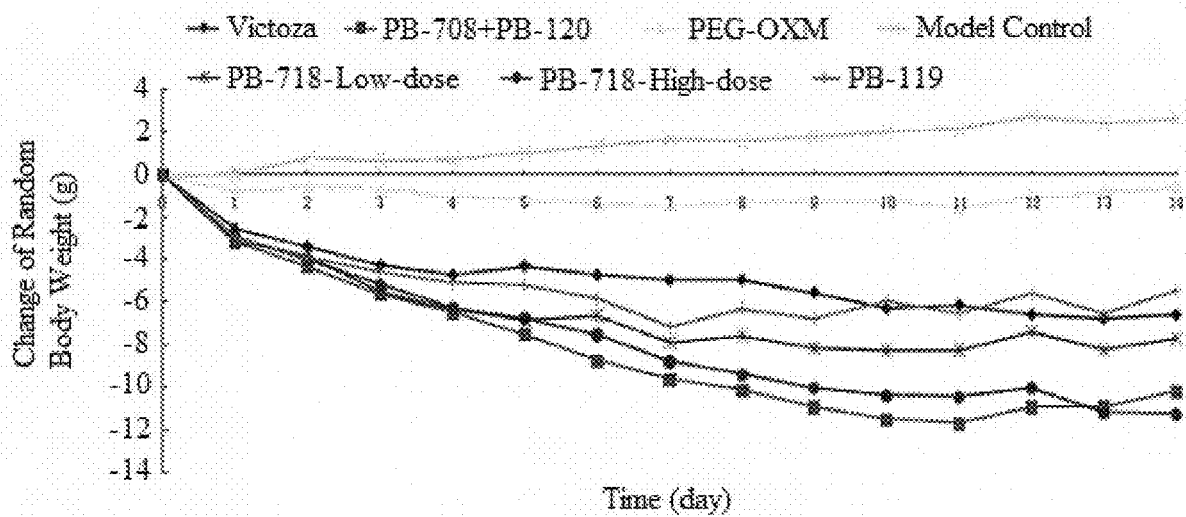
FIG. 12 shows the effect of continuous administration of compounds PB-718, PB-119 and combination (PB-708+PB-120) on body weight of DIO mice.
Figure 13:
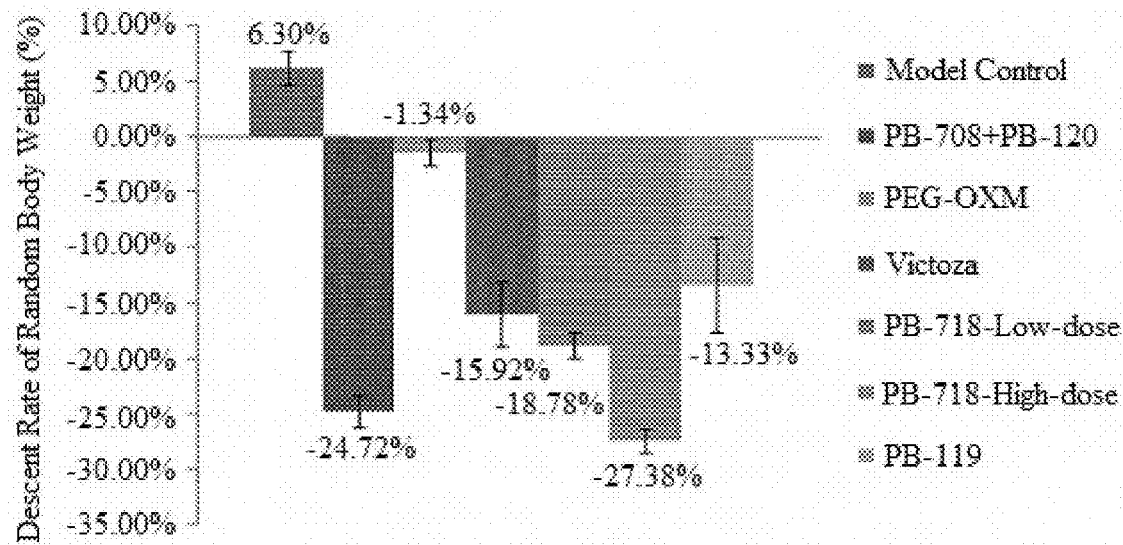
FIG. 13 shows the descent rate of body weight of DIO mice after continuous administration of compounds PB-718, PB-119 and combination (PB-708+PB-120).

The effect of long-term administration on body weight of DIO mice was shown in FIG. 12 and FIG. 13. At the end of the experiment, the body weight of the model control group increased by 6.30% compared with that before the administration, and the body weight of each treatment group was decreased at different degrees. Among them, the Victoza group lost 15.92% ($p<0.05$) of weight compared with that before the administration; the PB-119 group lost 13.33% ($p<0.05$), similar to the Victoza group. The PEG-OXM group only decreased by 1.34% ($p>0.05$), probably due to the fact that the natural dual agonist Oxyntomodulin has weak activity to glucagon and GLP-1 receptor. The body weight of the combinational administration group decreased by 24.72% compared with that before the administration, showing statistically significant difference ($p<0.001$) compared with the model control group. PB-718 showed a dose-dependent effect on weight loss in DIO mice. PB-718 low-dose group lost 18.78% of body weight ($p<0.001$), while PB-718 high-dose group lost 27.38% of body weight ($p<0.001$). The experiment results show that the dual agonist PB-718 for glucagon and GLP-1 receptor, as well as the long-term combinational administration of glucagon+GLP-1 receptor agonist, has obvious inhibitory effect on the body weight of DIO mice, of which the weight loss effect was significantly better than that of the GLP-1 receptor agonist PB-119 alone.

Figure 14:
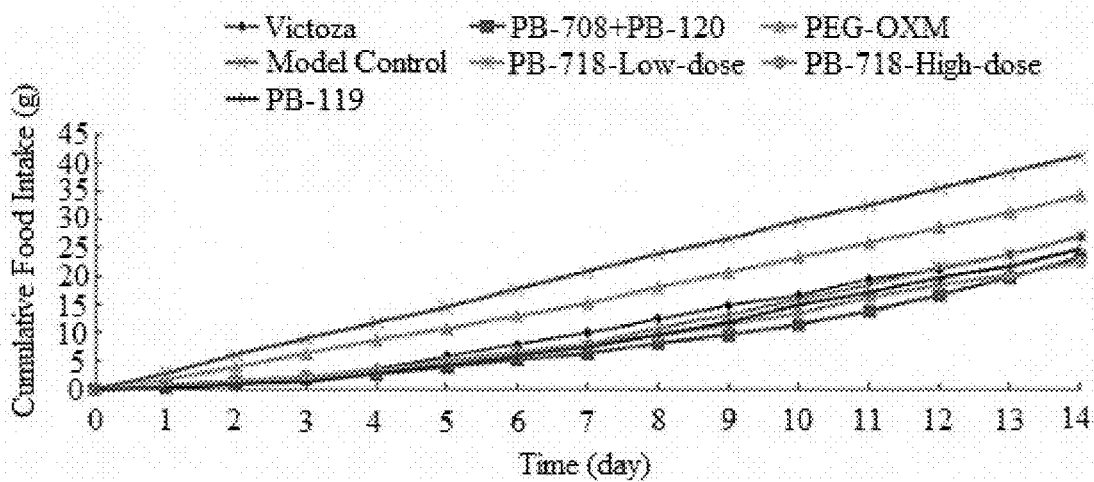
FIG. 14 shows the effect of long-term administration of compounds PB-718, PB-119 and combination (PB-708+PB-120) on cumulative food intake of DIO mice.
Figure 15:
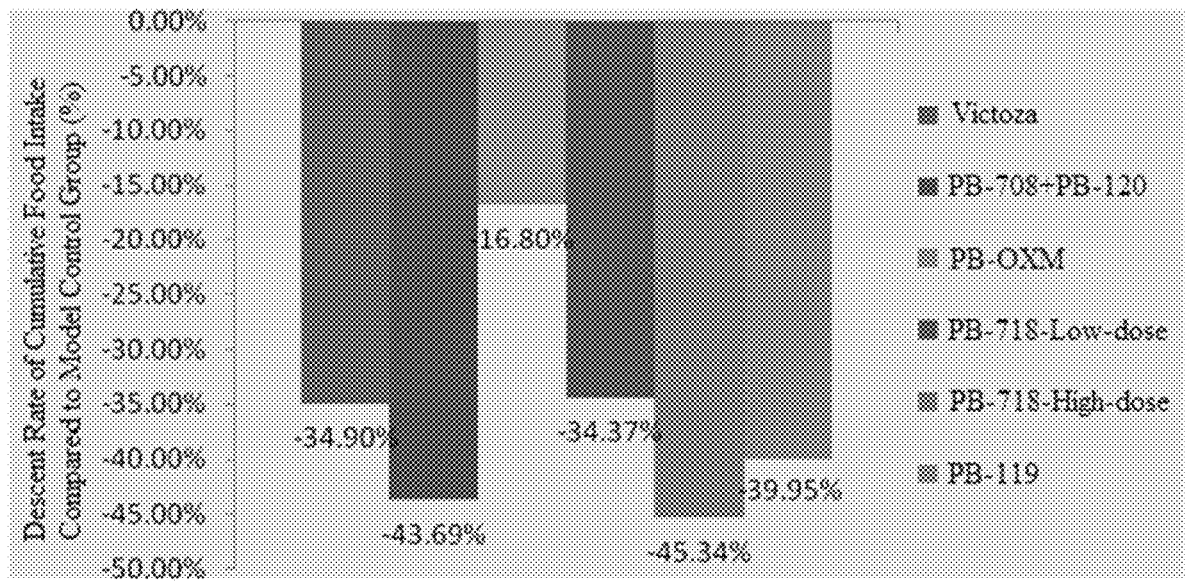
FIG. 15 shows the descent rate of cumulative food intake after administration for 14 consecutive days.

The effect of long-term administration on food intake of DIO mice is shown in FIG. 14 and FIG. 15. During the experiment, the cumulative food intake of the model control group showed a linear upward trend, while the treatment groups had a different degree of decline in food intake compared with the control group. At the end of the 14-day continuous administration, the cumulative food intake of the combinational administration group and PB-718 high-dose group decreased the most, by up to 43.69% and 45.34%, respectively. The cumulative food intake of PB-718 low-dose group and PB-119 group also decreased by 34.37% and 39.95%, respectively.

Figure 16:
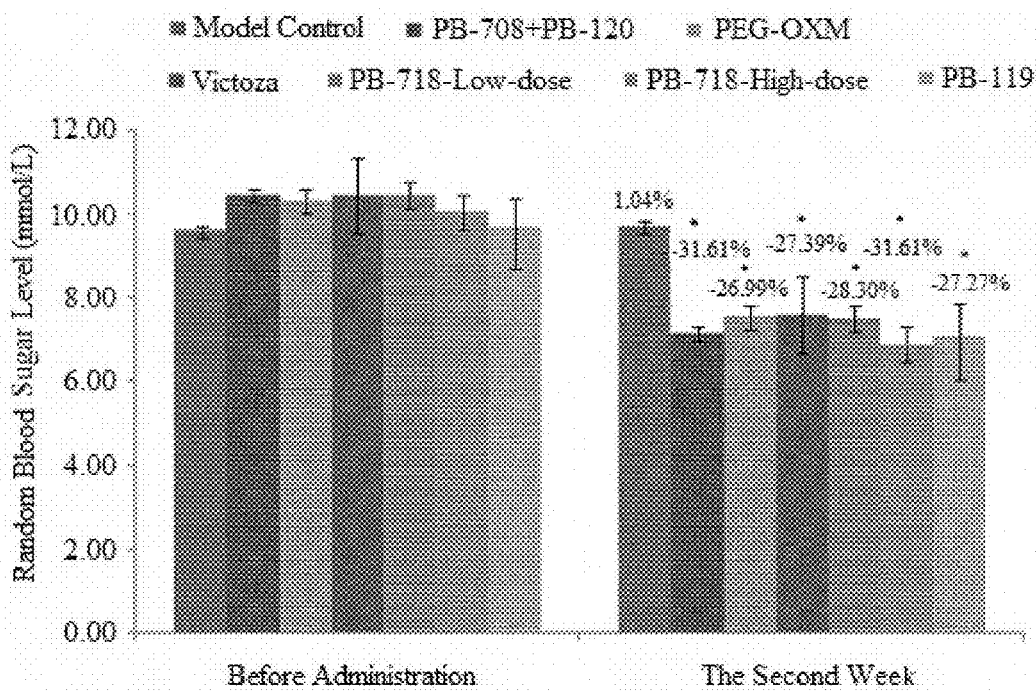
FIG. 16 shows the effect of continuous administration of compounds PB-718, PB-119 and combination (PB-708+PB-120) on random blood sugar level of DIO mice.

The effect of long-term administration on random blood sugar level of DIO mice was showed in FIG. 16. After 12 weeks of high-fat feeding, random blood sugar level of C57BL/6 mice increased to a certain degree. The average random blood sugar level in the normal feeding group was 8.7 mmol/L, while the average random blood sugar level in the high-fat feeding group increased by 17.3%, up to 10.2 mmol/L. The random blood sugar level of each treatment group decreased significantly after administration, and blood sugar level of PB-718 high-dose group, combinational administration group, PB-119 and PB-718 low-dose groups decreased by 31.61%, 31.61%, 27.27% and 28.30%, respectively, which showed statistically significant difference ($p<0.05$) from the model control group, indicating that long-term administration of compound PB-718 has a certain hypoglycemic effect on DIO mice.

Example 18. Experiment for Pharmacological Effect of Long-Term Administration of the Combination of PB-119 and PB-721 or the Combination of PB-119 and PB-722 on Weight Loss in DIO Mice Male C57BL/6 mice (Cavens Lab Animal Co., Ltd., Changzhou, China) were fed with high-fat diet (MD12032, 45% kcal, Medicience Co., Ltd., Jiangsu, China) for 16 weeks, of which the body weight was 20% more than the mice fed with common diet (Suzhou Shuangshi Animal Feed Technology Co., Ltd., China), indicating that the model of obesity-induced obesity (DIO) was successfully established. 80 DIO mice were divided into 10 groups based on their body weight and random blood sugar level, with 8 mice per group, which were model control group, PB-119 (10 nmol/kg) group, PB-721 (60 nmol/kg) group, PB-722 (60 nmol/kg) group, PB-722 (10 nmol/kg)+PB-119 (10 nmol/kg) group, PB-722 (30 nmol/kg)+PB-119 (10 nmol/kg) group, PB-722 (60 nmol/kg)+PB-119 (10 nmol/kg) group, PB-722 (100 nmol/kg)+PB-119 (10 nmol/kg) group, PB-722 (150 nmol/kg)+PB-119 (10 nmol/kg) group, PB-721 (60 nmol/kg)+PB-119 (10 nmol/kg) group and model control group (physiological saline). Each group was administered subcutaneously, once every two days, and the experiment lasted for 21 days with 11 administrations. During the experimental period, the body weight and food intake of the mice were measured every day. The blood sugar level was measured at Day1 and Day21, and the serum triglyceride serum, total cholesterol, liver triglyceride and other indexes were measured at Day21.

Figure 17:
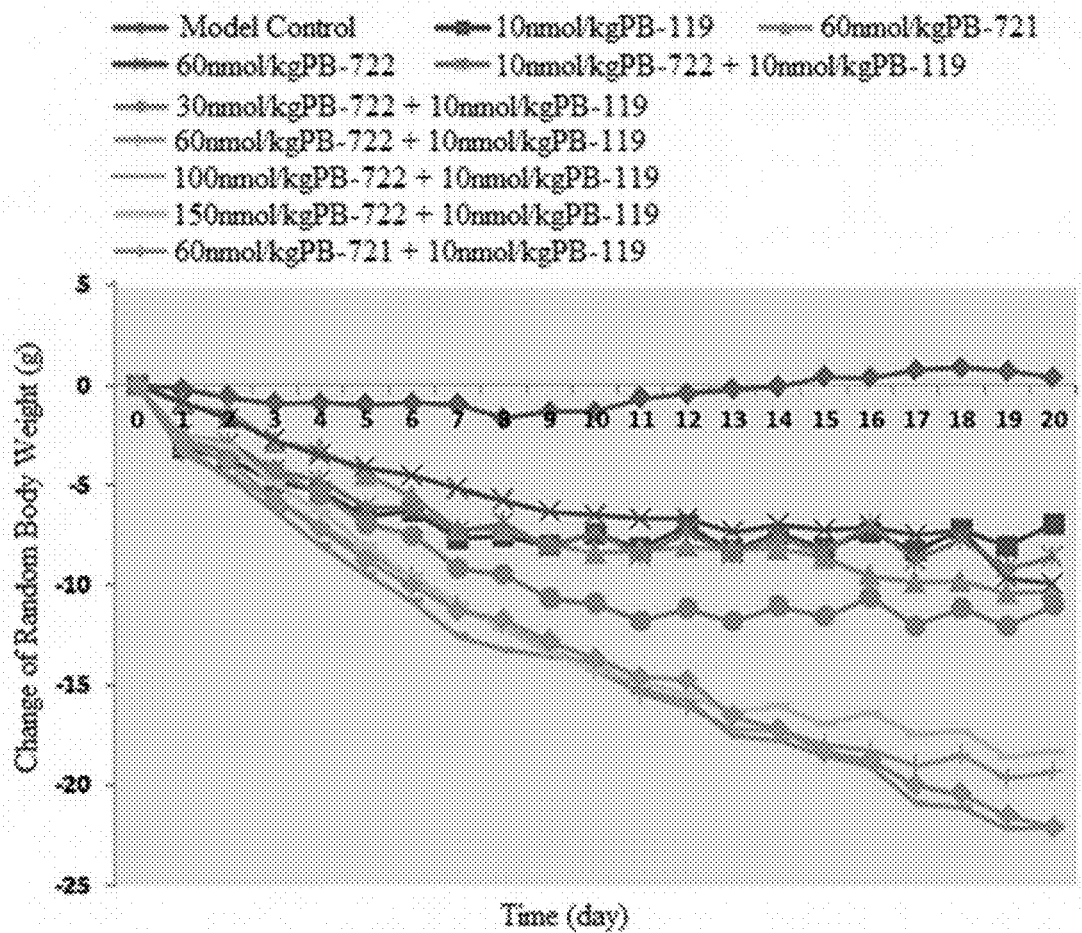
FIG. 17 shows the effect of long-term administration on random body weight of DIO mice.
Figure 18:
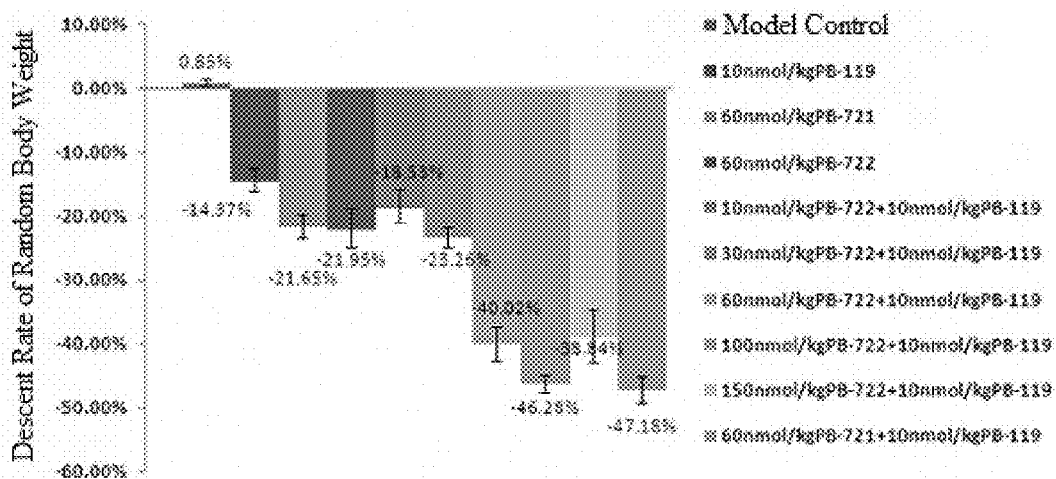
FIG. 18 shows the descent rate of random body weight of DIO mice after long-term administration.

The effect of long-term administration on body weight of DIO mice was shown in FIG. 17 and FIG. 18. During the experiment, the body weight of the model control group was stable, and the body weight of each treatment group was decreased at different degrees. After the administration, the body weight of the model control group increased by 0.85% compared with that before the administration. The body weight of PB-119 alone group (10 nmol/kg) decreased by 14.37%, and the body weights of the PB-721 (60 nmol/L) and PB-722 (60 nmol/L) alone groups decreased by 21.65% and 21.95%, respectively. However, in the case of equal doses, mice in the combinational administration groups (10 nmol/kg PB-119+60 nmol/kg PB-721) and (10 nmol/kg PB-119+60 nmol/kg PB-722) have a body weight decrease of 47.18% and 40.02%, respectively, and the body weight loss rate exceeded the sum of the rate caused by the administration of the two components in the combination alone, demonstrating that the simultaneous use of the two components of the combination has a synergistic effect on the weight loss of DIO mice.

In addition, the inventors have surprisingly found that when the molar ratio of GLP-1 receptor agonist (i.e., PB-119) and glucagon receptor agonist (i.e., PB-722) is within a certain range, the weight loss effect is surprisingly good. See the data of PB-722 (60 nmol/kg)+PB-119 (10 nmol/kg) group, PB-722 (100 nmol/kg)+PB-119 (10 nmol/kg) group, PB-722 (150 nmol/kg)+PB-119 (10 nmol/kg) group.

Figure 19:
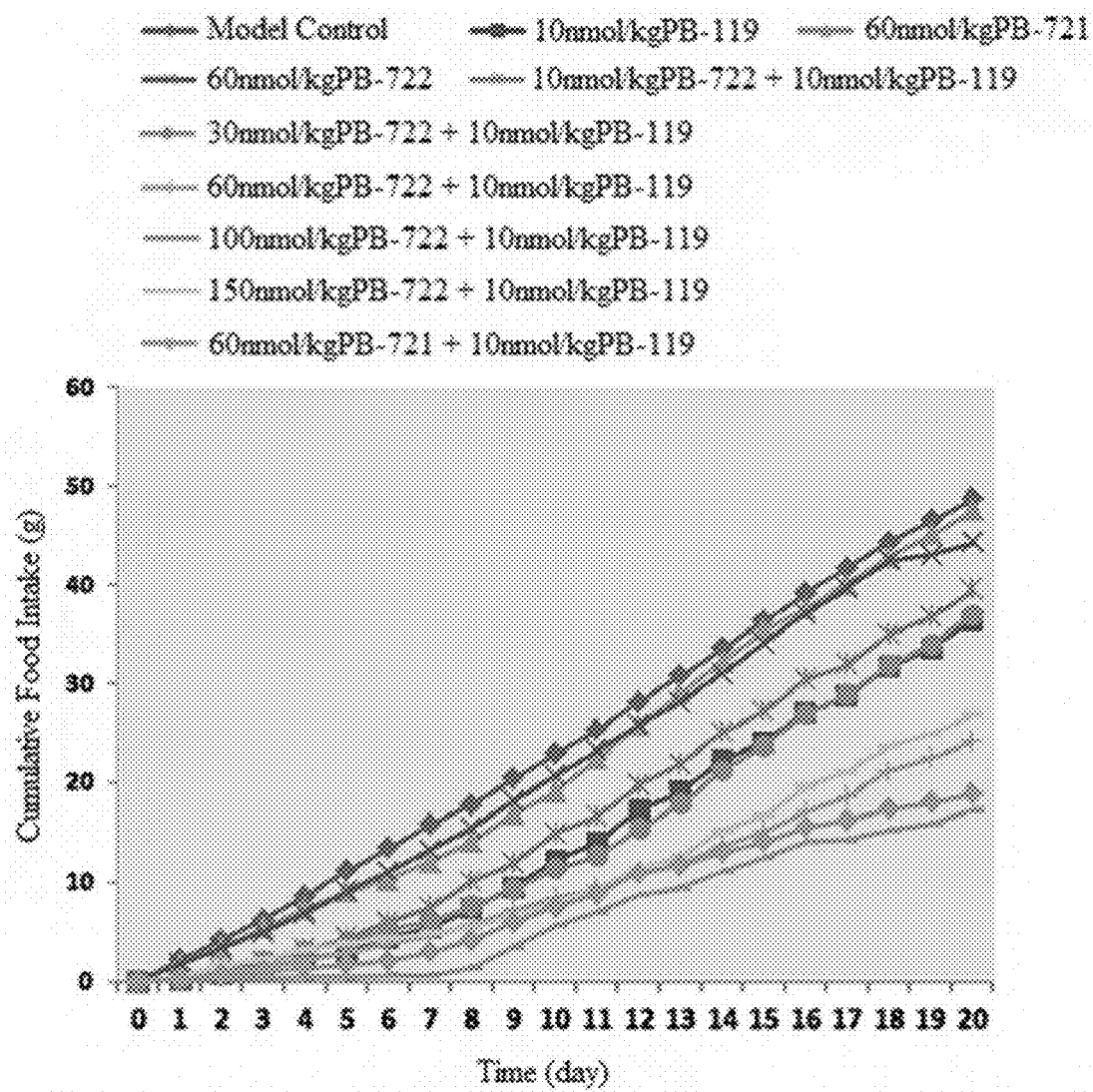
FIG. 19 shows the effect of long-term administration on food intake of DIO mice.
Figure 20:
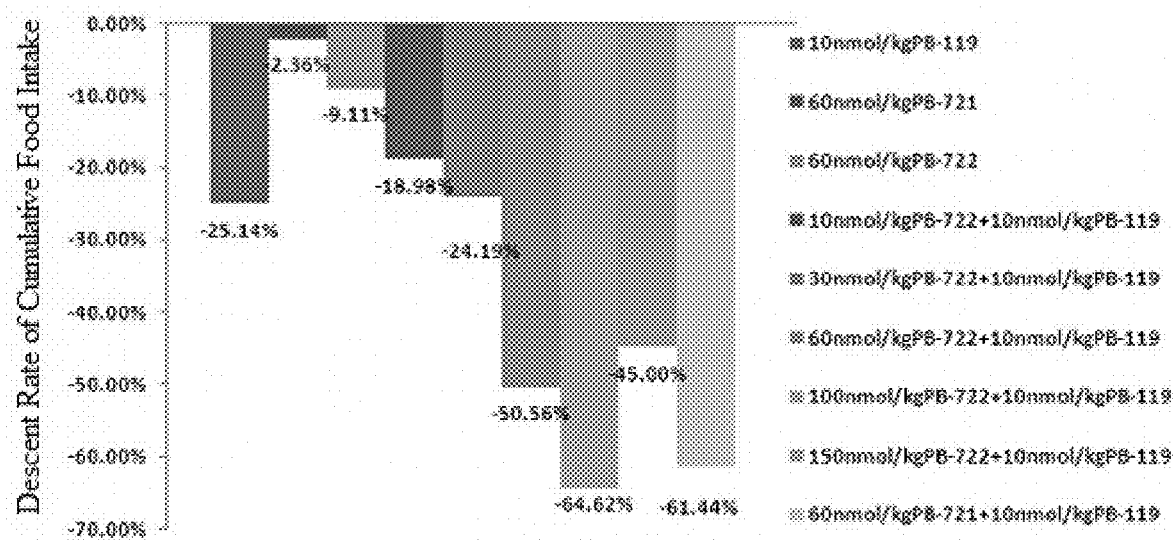
FIG. 20 shows the descent rate of cumulative food intake after long-term administration.

The effect of long-term administration on food intake of DIO mice is shown in FIG. 19 and FIG. 20. PB-119, PB-721 and PB-722 alone has a certain inhibitory effect on the appetite of DIO mice, while the combination of PB-119 and PB-721 or the combination of PB-119 and PB-722 have strong inhibitory effect on the appetite of DIO mice, which was more prominent than the sum of the inhibitory effect achieved by administration of the two components alone. Compared with the model control group, the cumulative food intake of PB-119 (10 nmol/kg) alone, PB-721 (60 nmol/kg) alone and PB-722 (60 nmol/kg) alone groups decreased by 25.14%, 2.36% and 9.11%, respectively. The cumulative food intake of combinational administration group (10 nmol/kg PB-119+60 nmol/kg PB-721) decreased by 61.44% and the cumulative food intake of combinational administration group (10 nmol/kg PB-119+60 nmol/kg PB-722) decreased by 50.56%.

Figure 21:
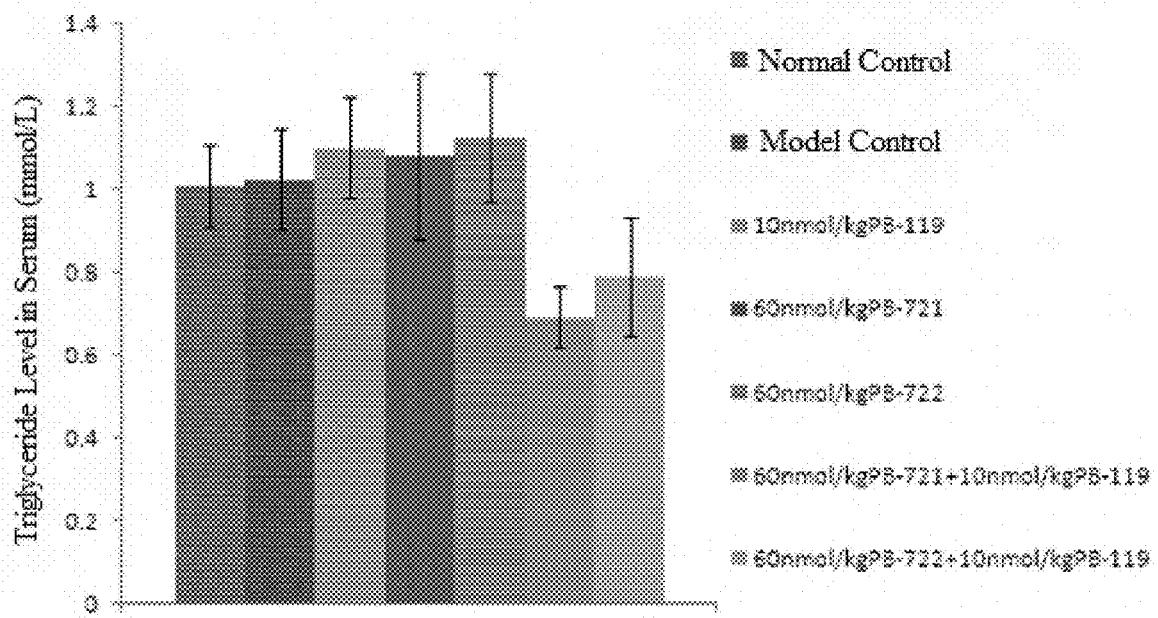
FIG. 21 shows the effect of long-term administration on triglyceride level in the serum of DIO mice.
Figure 22:
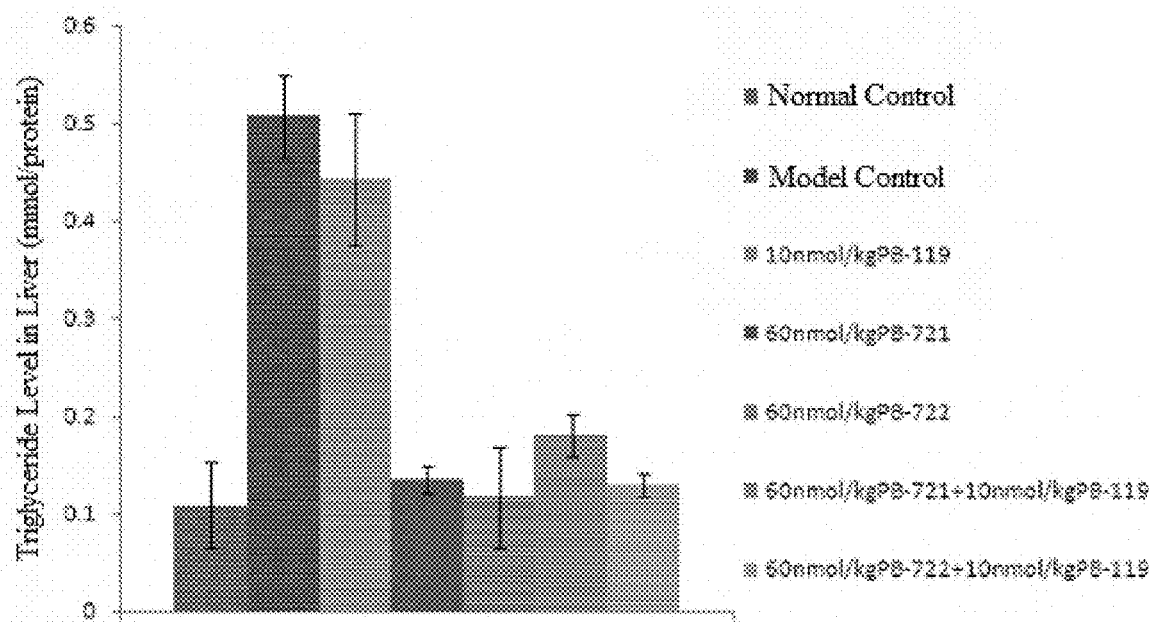
FIG. 22 shows the effect of long-term administration on triglyceride level in the liver of DIO mice.
Figure 23:
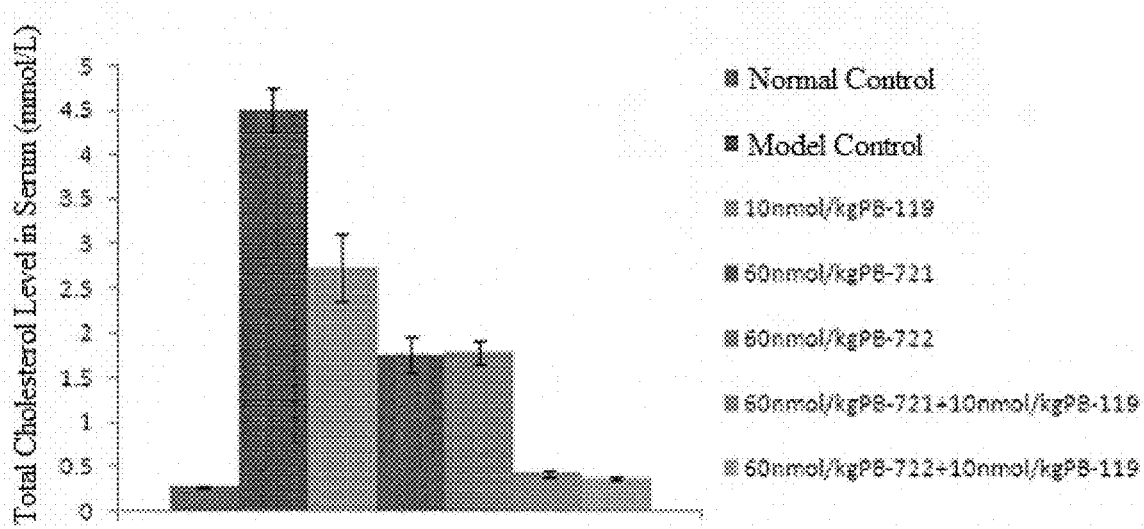
FIG. 23 shows the effect of long-term administration on total cholesterol level in the serum of DIO mice.

The results of serum triglyceride, serum total cholesterol and liver triglyceride are shown in FIG. 21, FIG. 22 and FIG. 23. The total cholesterol and liver triglyceride levels in the model control DIO mice group were significantly higher than those of the normal control group, indicating a clear disorder of lipid metabolism. The long-term administration of PB-119 (10 nmol/kg), PB-721 (60 nmol/kg) or PB-722 (60 nmol/kg) alone did not significantly improve the serum triglyceride level in DIO mice. The serum triglyceride level in the combinational administration of PB-119 and PB-721 or PB-119 and PB-722 groups at equal dose significantly decreased (p<0.05) by 32.58% and 22.83%, respectively, compared with that of the model control group.

The liver triglyceride content of DIO mice was significantly higher than that of normal control mice (p<0.01). Compared with the model control group, the liver triglyceride content of PB-119 (10 nmol/kg) alone group decreased by 12.67% (p>0.05); the liver triglyceride contents of PB-721 (60 nmol/kg) alone group, PB-722 (60 nmol/kg) alone group and two combinational administration groups significantly (p<0.01) decreased by 73.29%, 76.84%, 64.47% and 74.48%, respectively, which was close to the liver triglyceride level in normal control mice.

Serum total cholesterol content of DIO mice was significantly higher than that of normal control mice (P<0.001). Serum total cholesterol contents in the long-term administration of PB-119 (10 nmol/kg) alone group, PB-721 (60 nmol/kg) alone group and PB-722 (60 nmol/kg) alone group of DIO mice decreased (p<0.05) by 39.35%, 60.86% and 60.56%, respectively. The serum total cholesterol content in the combinational administration of PB-119 and PB-721 group or PB-119 and PB-722 group significantly decreased (p<0.001) by 90.85% and 91.88%, respectively.

Example 19. Experiment for Pharmacological Effect on Weight Loss in Cynomolgus Monkeys with Diet-Induced Obesity 14 cynomolgus monkeys with diet-induced obesity (purchased from Jingang Biotechnology Co. Ltd., Hainan, China; diet-induced obesity model established by WuXi Apptec Co. Ltd., Shanghai, China; Body Mass Index BMI>35) were randomly divided into 4 groups, with 1 monkey per gender in blank control group and 2 monkeys per gender in treatment group: blank control group (0.9% physiological saline), low-dose group (the composition of the present disclosure), medium-dose group (the composition of the present disclosure) and high-dose group (the composition of the present disclosure). Animals in each group were administered subcutaneously once every 4 days for 8 consecutive times. During the experiment, the animals were observed twice a day for the general status, behavior, activity, excretion, respiration, and other abnormal symptoms. The amount of food intake was measured every day, body weight was measured every 4 days, and blood samples were taken to measure blood biochemical indicators at Day 1 (before administration) and Day 32 (after administration).

In the experiment, except for the weight loss and food intake reduction, all experimental animals were well tolerated and showed no other abnormalities.

Figure 24:
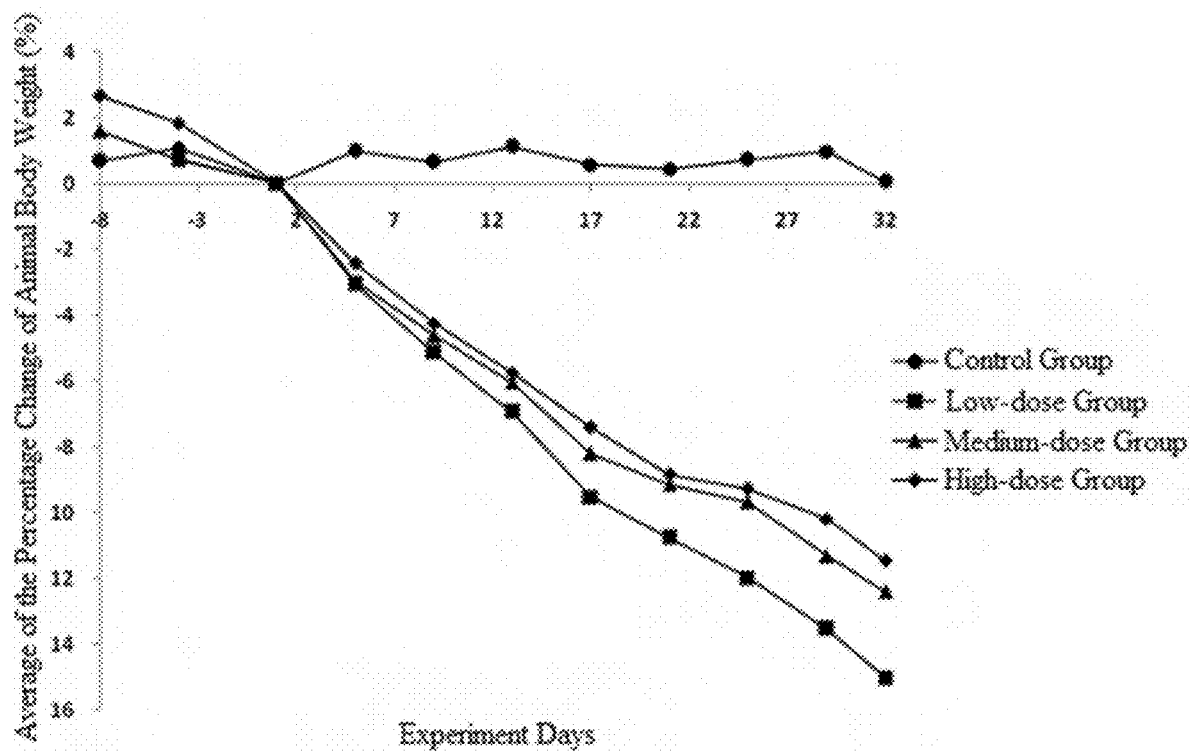
FIG. 24 shows the effect of long-term administration of the composition of the present disclosure on the body weight of obese cynomolgus monkeys.

The effect of long-term administration of the composition of the present disclosure on the body weight of obese cynomolgus monkeys was shown in FIG. 24. During the experiment, the body weight of the blank control group was stable, and the body weight of each treatment group decreased at different degrees. After the administration, the body weight of the blank control group increased by 0.065% compared with that before the administration, and the weight loss percentages of the low-dose group, medium-dose group and high-dose group were 15.0%, 12.4% and 11.5%, respectively.

Figure 25:
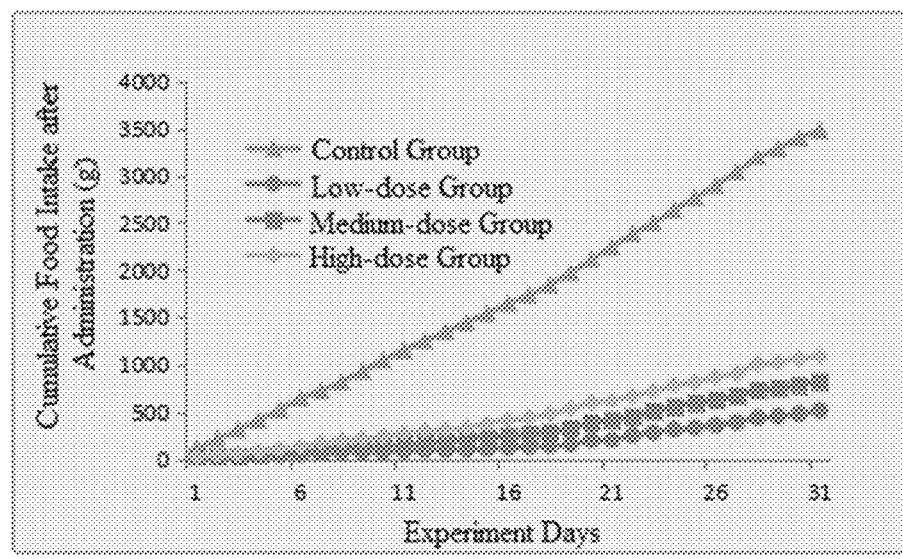
FIG. 25 shows the effect of long-term administration of the composition of the present disclosure on cumulative food intake of obese cynomolgus monkeys.
Figure 26:
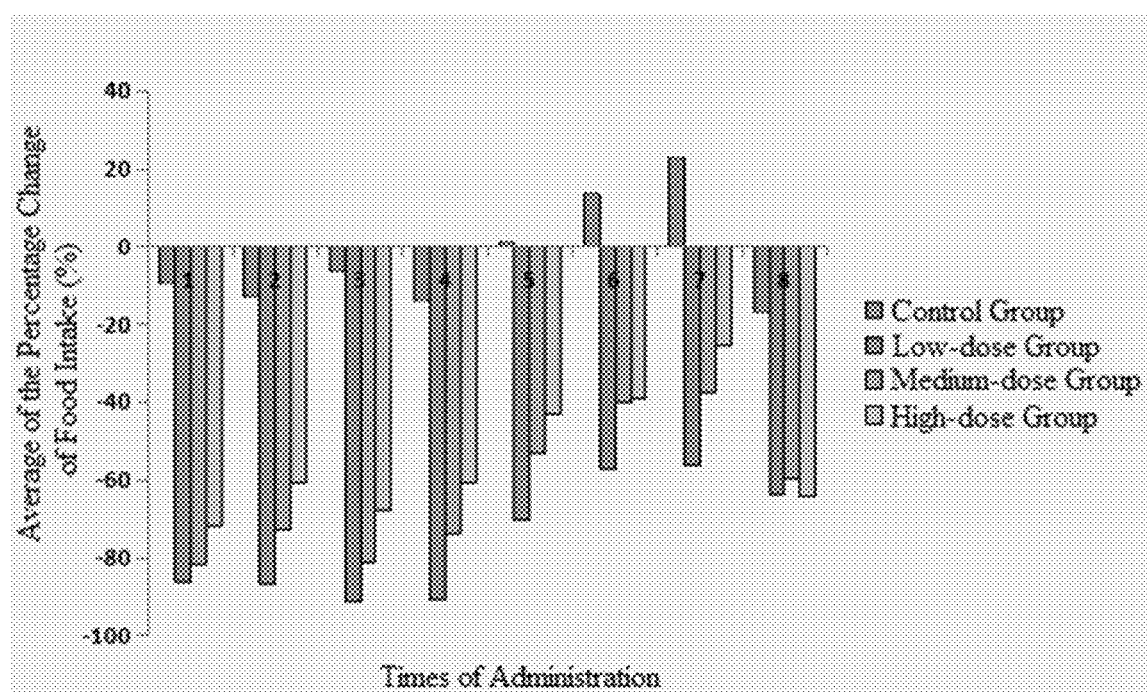
FIG. 26 shows a histogram of the percentage change in the average food consumption after long-term administration of the composition of the present disclosure—the number of administration in cynomolgus monkeys.

The effect of long-term administration on the food intake of diet-induced obesity in cynomolgus monkeys was shown in FIG. 25 and FIG. 26. After administration once every 4 days for 8 consecutive times, the food intake of each treatment group was remarkably decreased. Before and after the administration, the food intake of the blank control group decreased by only 2.33%, while the food intakes of low-dose group, medium-dose group and high-dose group decreased 75.6%, 62.5% and 53.7%, respectively.

The above results show that the composition of the present disclosure can significantly reduce the body weight of the subject and significantly suppress appetite of the subject.

Figure 27:
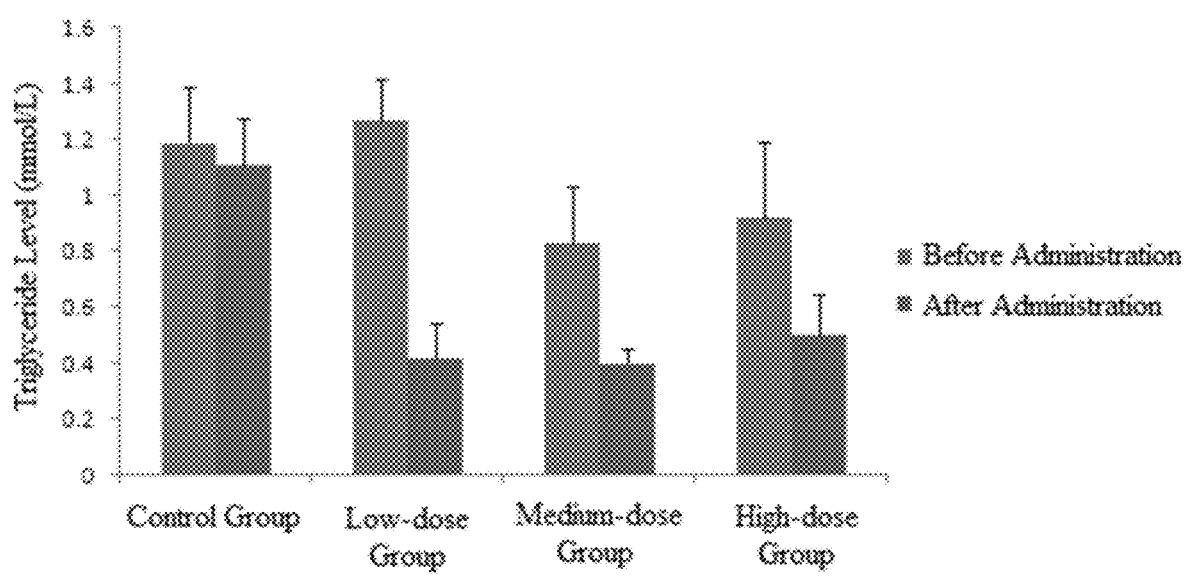
FIG. 27 shows the effect of long-term administration of the composition of the present disclosure on the triglyceride level in the serum of the cynomolgus monkeys.
Figure 28:
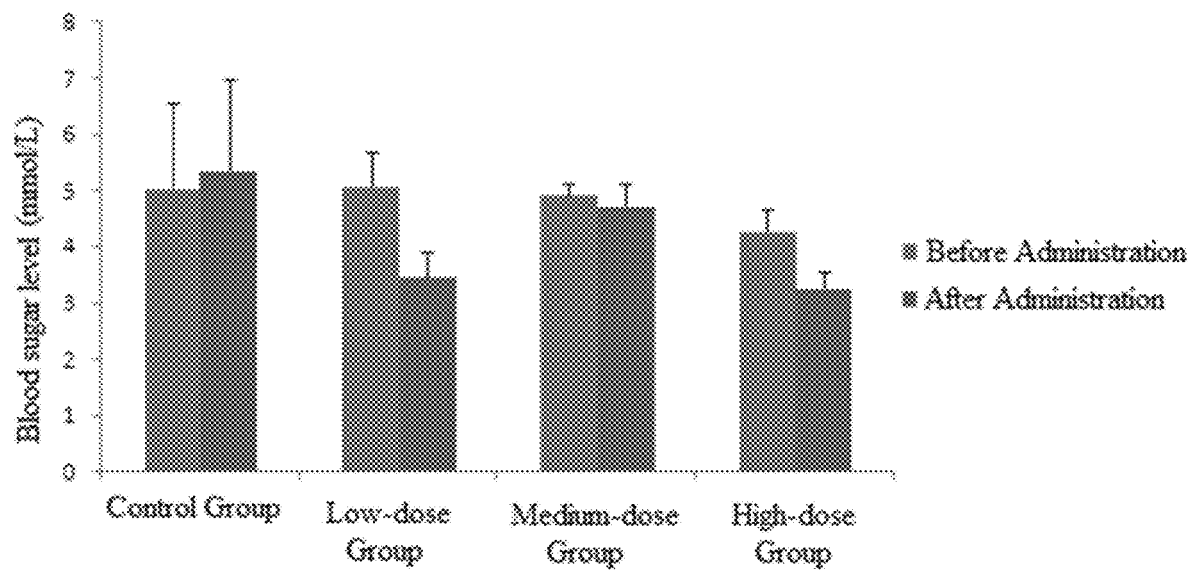
FIG. 28 shows the effect of long-term administration of the composition of the present disclosure on the serum glucose level of the cynomolgus monkeys.
Figure 29:
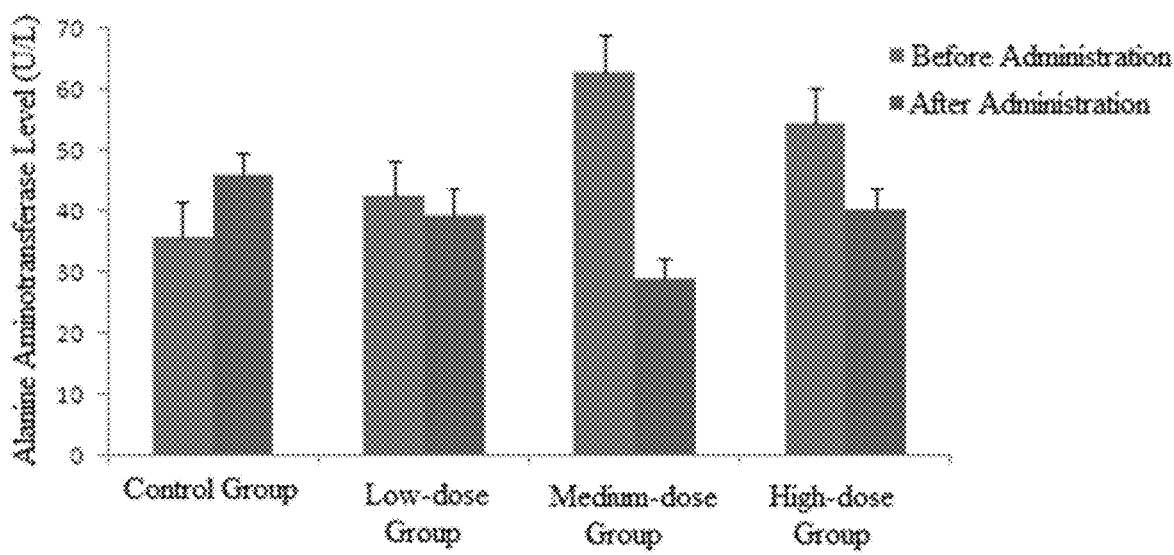
FIG. 29 shows the effect of long-term administration of the composition of the present disclosure on the serum alanine aminotransferase level of the cynomolgus monkeys.

The blood biochemical results of experimental animals are shown in Table 3. The average values of triglyceride, glucose and alanine aminotransferase are shown in FIGS. 27, 28 and 29. Cynomolgus monkeys with diet-induced obesity were injected subcutaneously with the composition of the present disclosure once every 4 days for 8 consecutive weeks. Before and after the administration, serum triglyceride, serum glucose and serum alanine aminotransferase decreased, while in the blank control group, there was little change in triglyceride, glucose and alanine aminotransferase levels were slightly elevated. There was no abnormality in blood biochemical experiments of low-dose group, medium-dose group and high-dose group.

TABLE 3

Cynomolgus monkeys with diet-induced obesity were injected subcutaneously with the composition of the present disclosure for 8 consecutive times. Blood biochemical indicators before and after the administration were shown.

| | | Group | | | | | | | |
|---|---|---|---|---|---|---|---|---|---|
| | | 1 (Control Group) | | 2 (Low-dose Group) | | | | 3 (Medium-dose Group) | |
| | | Gender | | | | | | | |
| | | Male | Female | Male | | Female | | Male | |
| | | Animal No. | | | | | | | |
| | | C1001 | C1502 | C2001 | C2002 | C2503 | C2504 | C3001 | C3002 |
| Total Cholesterol (mmol/L) | Before Administration | 2.36 | 2.72 | 2.18 | 2.84 | 2.80 | 2.81 | 2.78 | 2.22 |
| | After Administration | 2.36 | 2.21 | 2.79 | 2.92 | 2.88 | 2.24 | 2.97 | 1.70 |
| Triglyceride (mmol/L) | Before Administration | 0.91 | 1.46 | 1.53 | 1.26 | 1.03 | 0.57 | 0.70 | 0.49 |
| | After Administration | 1.25 | 0.97 | 0.42 | 0.22 | 0.63 | 1.05 | 0.45 | 0.31 |
| Glucose (mmol/L) | Before Administration | 3.18 | 6.95 | 5.05 | 3.87 | 6.36 | 9.14 | 4.88 | 3.46 |
| | After Administration | 3.25 | 7.48 | 3.36 | 2.52 | 4.51 | 5.61 | 3.83 | 3.32 |
| Total Bilirubin (umol/L) | Before Administration | 2.46 | 2.69 | 2.49 | 5.16 | 2.65 | 3.39 | 3.38 | 3.18 |
| | After Administration | 2.15 | 3.43 | 5.33 | 5.77 | 3.98 | 11.69 | 6.05 | 3.84 |
| Alanine Aminotransferase (U/L) | Before Administration | 30 | 41 | 41 | 60 | 26 | 20 | 73 | 24 |
| | After Administration | 42 | 50 | 18 | 50 | 50 | 19 | 22 | 29 |
| Aspartate Aminotransferase (U/L) | Before Administration | 29 | 26 | 40 | 37 | 28 | 33 | 64 | 39 |
| | After Administration | 34 | 27 | 30 | 40 | 30 | 40 | 44 | 40 |
| Total Protein (g/L) | Before Administration | 81.2 | 85.3 | 76 | 90 | 88 | 75.5 | 81.8 | 86.5 |
| | After Administration | 80.4 | 81 | 70.5 | 82.2 | 83.2 | 68.5 | 79.1 | 80.6 |
| Albumin (g/L) | Before Administration | 41.5 | 42.5 | 40.4 | 46.9 | 37.2 | 38.4 | 41 | 43.2 |
| | After Administration | 40.3 | 41.2 | 35.5 | 45 | 38.9 | 31.1 | 43 | 41.7 |
| Alkaline Phosphatase (U/L) | Before Administration | 116 | 153 | 162 | 145 | 94 | 238 | 180 | 162 |
| | After Administration | 115 | 114 | 162 | 122 | 80 | 474 | 128 | 130 |
| Glutamyl Transpeptidase (U/L) | Before Administration | 46 | 87 | 25 | 77 | 52 | 79 | 102 | 87 |
| | After Administration | 45 | 77 | 22 | 74 | 49 | 58 | 86 | 96 |
| Globulin (g/L) | Before Administration | 39.7 | 42.8 | 35.6 | 43.1 | 50.8 | 37.1 | 40.8 | 43.3 |
| | After Administration | 40.1 | 39.8 | 35 | 37.2 | 44.3 | 37.4 | 36.1 | 38.9 |
| Albumin/Globulin | Before Administration | 1.05 | 0.99 | 1.13 | 1.09 | 0.73 | 1.04 | 1 | 1 |
| | After Administration | 1.00 | 1.04 | 1.01 | 1.21 | 0.88 | 0.83 | 1.19 | 1.07 |
| Urea (mmol/L) | Before Administration | 4.30 | 5.14 | 4.31 | 4.44 | 5.42 | 4.34 | 5.11 | 5.32 |
| | After Administration | 4.37 | 6.16 | 4.44 | 7.08 | 5.28 | 6.99 | 5.25 | 5.39 |
| Creatinine (mmol/L) | Before Administration | 81.0 | 51.0 | 93.0 | 109 | 65.0 | 50 | 119 | 82 |
| | After Administration | 72.0 | 46.0 | 77.0 | 104 | 60.0 | 48 | 108 | 75 |
| Creatine Kinase (U/L) | Before Administration | 149 | 151 | 112 | 213 | 86.0 | 96 | 150 | 96 |
| | After Administration | 294 | 151 | 59 | 153 | 79.0 | 186 | 96 | 92 |
| Calcium (mmol/L) | Before Administration | 2.42 | 2.44 | 2.41 | 2.58 | 2.36 | 2.49 | 2.49 | 2.54 |
| | After Administration | 2.43 | 2.33 | 2.31 | 2.46 | 2.45 | 2.38 | 2.37 | 2.47 |
| Phosphorus (mmol/L) | Before Administration | 1.44 | 1.73 | 1.46 | 1.8 | 1.01 | 2.03 | 1.58 | 1.87 |

TABLE 3-continued

Cynomolgus monkeys with diet-induced obesity were injected subcutaneously with the composition of the present disclosure for 8 consecutive times. Blood biochemical indicators before and after the administration were shown.

|  |  |  |  |  |  |  |  |  |
|---|---|---|---|---|---|---|---|---|
|  | After Administration | 1.6 | 1.62 | 1.49 | 1.16 | 1.08 | 1.94 | 1.3 | 1.56 |
| Sodium (mmol/L) | Before Administration | 145 | 150 | 148 | 151 | 143 | 149 | 149 | 150 |
|  | After Administration | 143 | 146 | 141 | 144 | 142 | 141 | 145 | 146 |
| Potassium (mmol/L) | Before Administration | 4.3 | 4.1 | 4.0 | 4.9 | 4.1 | 4.9 | 5.1 | 5.3 |
|  | After Administration | 4.6 | 4.9 | 4.8 | 5.1 | 4.5 | 5.9 | 4.1 | 6.6 |
| Chlorine (mmol/L) | Before Administration | 105 | 105 | 106 | 104 | 103 | 106 | 106 | 107 |
|  | After Administration | 104 | 111 | 103 | 106 | 107 | 101 | 105 | 110 |

| | | Group | | | | | |
|---|---|---|---|---|---|---|---|
| | | 3 (Medium-dose Group) | | 4 (High-dose Group) | | | |
| | | Gender | | | | | |
| | | Female | | Male | | Female | |
| | | Animal No. | | | | | |
| | | C3503 | C3504 | C4001 | C4002 | C4503 | C4504 |
| Total Cholesterol (mmol/L) | Before Administration | 2.68 | 2.35 | 3.41 | 2.78 | 2.88 | 2.47 |
|  | After Administration | 2.53 | 3.00 | 4.17 | 3.50 | 2.81 | 2.55 |
| Triglyceride (mmol/L) | Before Administration | 0.61 | 1.51 | 0.30 | 1.46 | 0.30 | 1.60 |
|  | After Administration | 0.40 | 0.43 | 0.25 | 0.62 | 0.32 | 0.82 |
| Glucose (mmol/L) | Before Administration | 5.31 | 6.08 | 3.96 | 4.97 | 4.06 | 4.09 |
|  | After Administration | 4.91 | 6.87 | 2.99 | 2.91 | 3.77 | 3.39 |
| Total Bilirubin (umol/L) | Before Administration | 2.87 | 2.87 | 4.61 | 2.48 | 5.52 | 2.87 |
|  | After Administration | 3.87 | 4.71 | 4.13 | 3.72 | 8.08 | 4.46 |
| Alanine Aminotransferase (U/L) | Before Administration | 25 | 129 | 43 | 54 | 56 | 64 |
|  | After Administration | 23 | 42 | 18 | 35 | 42 | 65 |
| Aspartate Aminotransferase (U/L) | Before Administration | 31 | 53 | 48 | 41 | 44 | 40 |
|  | After Administration | 40 | 44 | 42 | 47 | 39 | 45 |
| Total Protein (g/L) | Before Administration | 89.4 | 85.6 | 82.6 | 88.5 | 90.2 | 79.5 |
|  | After Administration | 86.5 | 87 | 80.3 | 84.8 | 88.8 | 75 |
| Albumin (g/L) | Before Administration | 44.8 | 39.5 | 43 | 44.8 | 43.9 | 38.8 |
|  | After Administration | 44 | 43 | 43.3 | 44.6 | 43.1 | 39.6 |
| Alkaline Phosphatase (U/L) | Before Administration | 126 | 168 | 94 | 266 | 140 | 168 |
|  | After Administration | 98 | 123 | 119 | 193 | 110 | 124 |
| Glutamyl Transpeptidase (U/L) | Before Administration | 54 | 55 | 49 | 66 | 59 | 29 |
|  | After Administration | 59 | 35 | 64 | 52 | 55 | 26 |
| Globulin (g/L) | Before Administration | 44.6 | 46.1 | 39.6 | 43.7 | 46.3 | 40.7 |
|  | After Administration | 42.5 | 44 | 37 | 40.2 | 45.7 | 35.4 |
| Albumin/Globulin | Before Administration | 1 | 0.86 | 1.09 | 1.03 | 0.95 | 0.95 |
|  | After Administration | 1.04 | 0.98 | 1.17 | 1.11 | 0.94 | 1.12 |
| Urea (mmol/L) | Before Administration | 5.46 | 3.97 | 6.9 | 5.08 | 4.54 | 6.25 |

TABLE 3-continued

Cynomolgus monkeys with diet-induced obesity were injected subcutaneously with the composition of the present disclosure for 8 consecutive times. Blood biochemical indicators before and after the administration were shown.

| | | | | | | | |
|---|---|---|---|---|---|---|---|
| | After Administration | 7.74 | 6.33 | 4.88 | 5.3 | 3.95 | 4.07 |
| Creatinine (mmol/L) | Before Administration | 45 | 54 | 102 | 116 | 50 | 39 |
| | After Administration | 42 | 55 | 87 | 86 | 49 | 39 |
| Creatine Kinase (U/L) | Before Administration | 118 | 391 | 139 | 174 | 138 | 314 |
| | After Administration | 217 | 181 | 60 | 175 | 86 | 394 |
| Calcium (mmol/L) | Before Administration | 2.72 | 2.51 | 2.69 | 2.74 | 2.41 | 2.31 |
| | After Administration | 2.73 | 2.79 | 2.49 | 2.47 | 2.41 | 2.32 |
| Phosphorus (mmol/L) | Before Administration | 1.75 | 1.52 | 1.91 | 1.65 | 1.85 | 1.7 |
| | After Administration | 1.16 | 1.06 | 1.38 | 1.26 | 1.44 | 1.41 |
| Sodium (mmol/L) | Before Administration | 152 | 149 | 155 | 162 | 145 | 149 |
| | After Administration | 151 | 148 | 145 | 147 | 147 | 151 |
| Potassium (mmol/L) | Before Administration | 6.4 | 3.8 | 4.3 | 5.5 | 4.2 | 3.8 |
| | After Administration | 7.1 | 5.8 | 5.4 | 5.6 | 5.0 | 5.1 |
| Chlorine (mmol/L) | Before Administration | 106 | 103 | 104 | 114 | 103 | 105 |
| | After Administration | 112 | 110 | 106 | 110 | 112 | 115 |

Figure 30:
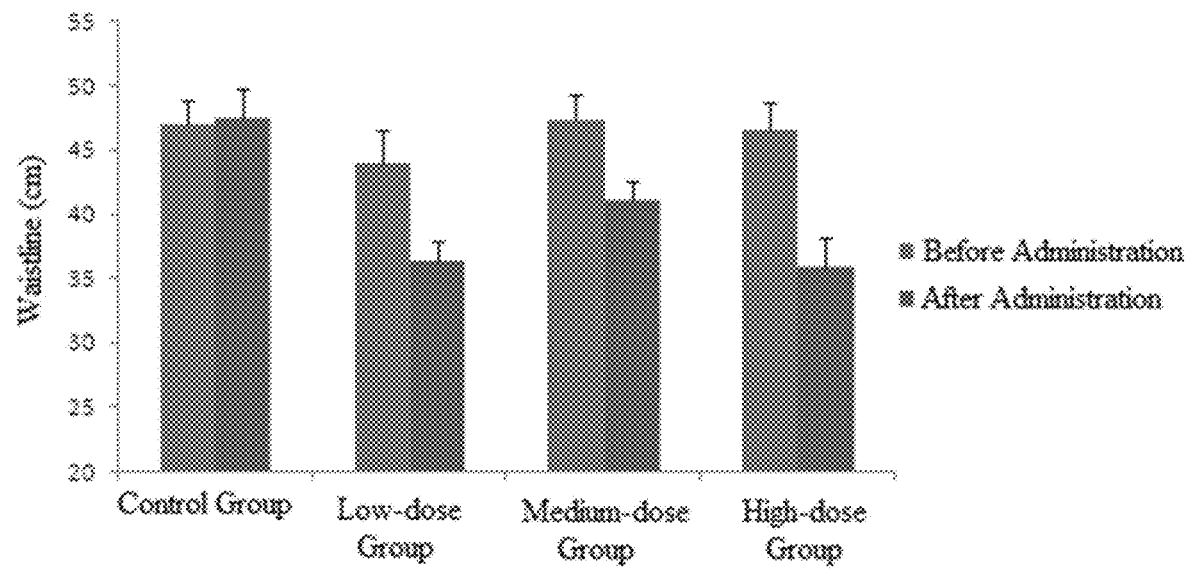
FIG. 30 shows the effect of long-term administration of the composition of the present disclosure on the waistline of the cynomolgus monkeys.
Figure 31:
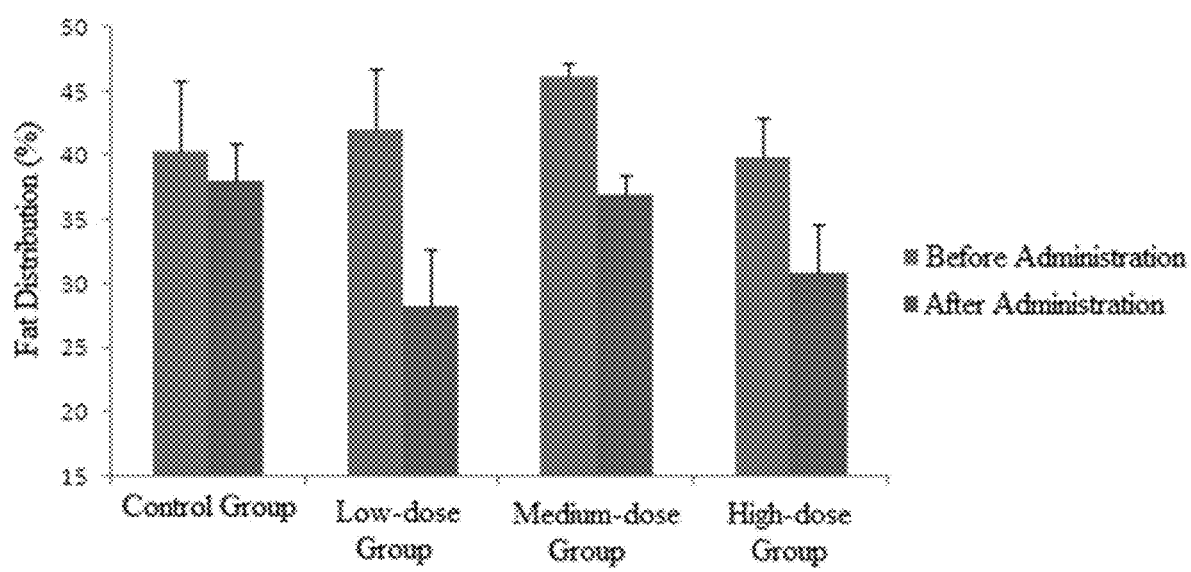
FIG. 31 shows the effect of long-term administration of the composition of the present disclosure on the fat distribution of the cynomolgus monkeys.

The effects of long-term administration on waistline and fat distribution of the cynomolgus monkeys with diet-induced obesity were shown in FIG. 30 and FIG. 31. After administration once every 4 days for 8 consecutive times, the waistline and fat distribution in all treatment groups significantly decreased, while the waistline and fat distribution of cynomolgus monkeys in the blank control group did not change significantly before and after administration.

Example 20. Experiment for Pharmacological Effect of the Combination of PB-119 and PB-722 on Weight Loss in DIO Mice Male C57BL/6 mice (from the same source as described above) were fed with high-fat diet (45% kcal) for 22 weeks. Their average body weight and blood sugar level were 20% higher compared with mice fed with common diets of the same age, indicating that the model of obesity and hyperglycemia was established successfully. 36 DIO mice were divided into 6 groups based on their body weight and random blood sugar level, with 6 mice per group. Group 1 was model control group, group 2 was 10 nmol/kg (42.03 μg/kg, based on peptide, the same below) PB-119 group, group 3 was 60 nmol/kg (212.58 μg/kg) PB-722 group, group 4 was 10 nmol/kg (42.03 μg/kg) PB-119 and 20 nmol/kg (70.86 μg/kg) PB-722 group, group 5 was 10 nmol/kg (42.03 μg/kg) PB-119 and 60 nmol/kg (212.58 μg/kg) PB-722 group, group 6 was 25 nmol/kg (75.02 μg/kg) liraglutide injection group. Except that administration was carried out twice a day in group 6, administration was carried out once every two days in other groups. The experiment was conducted for a total of 21 days for a continuous administration. The body weight and food intake of the mice were measured on the day of the administration, and random blood sugar level and fasting blood sugar level were measured on the second day after the last administration.

The results showed that continuous administration of combination (PB-119+PB-722) has a significant inhibitory effect on food intake and body weight of DIO mice.

Figure 32:
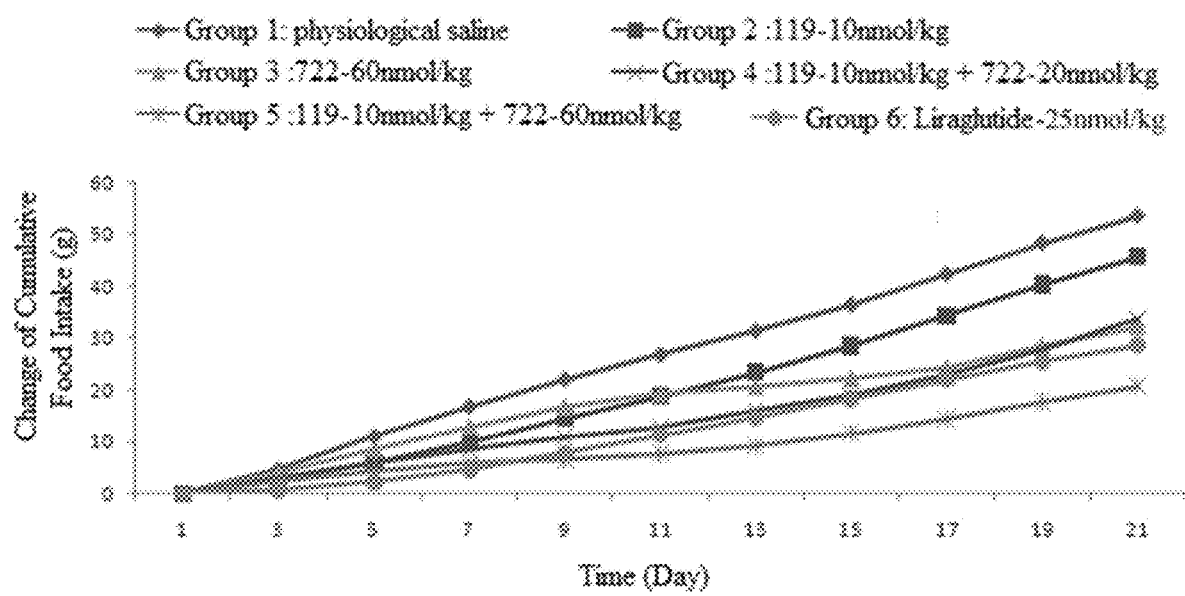
FIG. 32 shows the effect of continuous administration of combination (PB-119+PB-722) for 21 days on cumulative food intake of DIO mice.
Figure 33:
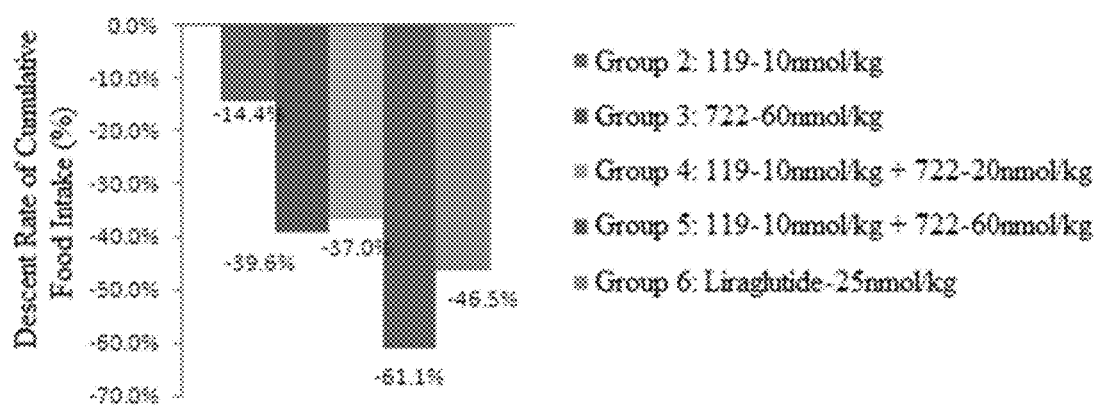
FIG. 33 shows the descent rate of cumulative food intake after continuous administration of combination (PB-119+PB-722) for 21 days compared to model control group.

Within 21 days after the start of continuous administration, the cumulative food intake of the model control group showed a linear upward trend, and the food intake of the combination groups decreased to various degrees compared with the control group. The results are shown in FIG. 32 and FIG. 33. At the end of the 21 days' continuous administration experiment, group 5: PB-722 (60 nmol/kg)+PB-119 (10 nmol/kg) showed the most decrease in cumulative food intake, reaching 61.1%, while PB-119 group had the least decrease in cumulative food intake, which was 14.4%.

Figure 34:
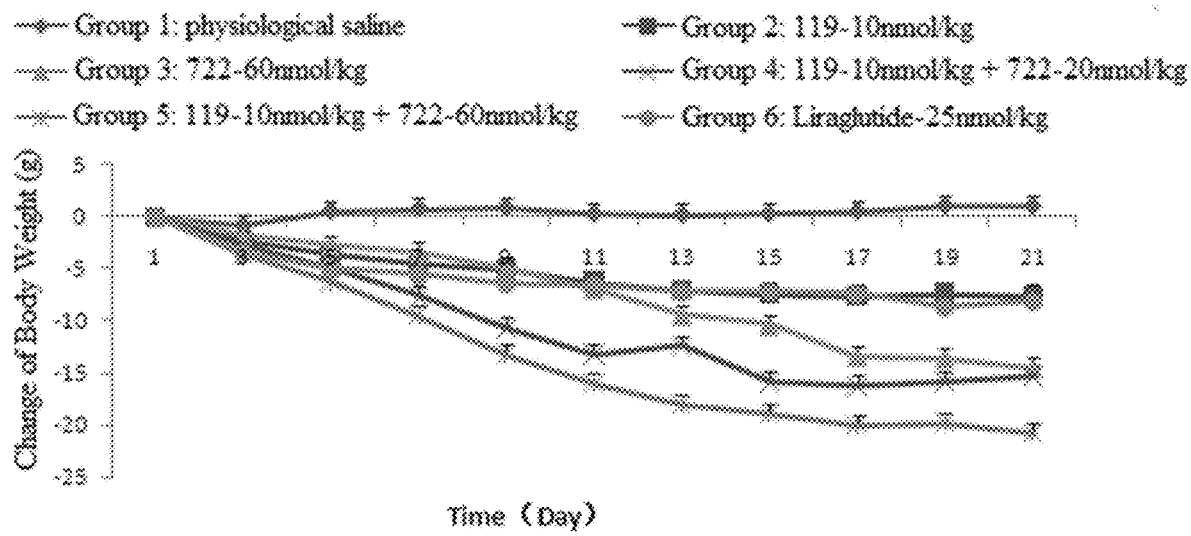
FIG. 34 shows the effect of continuous administration of combination (PB-119+PB-722) for 21 days on body weight of DIO mice.
Figure 35:
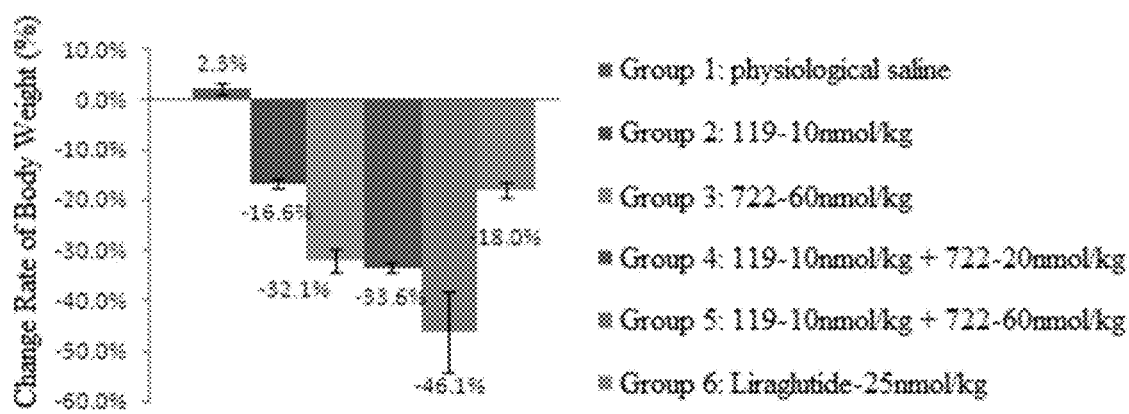
FIG. 35 shows the descent rate of body weight of DIO mice after continuous administration of combination (PB-119+PB-722) for 21 days.

The body weight of the model control group increased by 2.3% compared with that before the administration, while the body weight of the treatment groups showed decrease at various degrees. The results are shown in FIG. 34 and FIG. 35. The decrease of combination group PB-722 (60 nmol/kg)+PB-119 (10 nmol/kg) was the most significant, which was a 46.1% decrease compared with that before the administration, showing statistical significance compared with the model control group ($p<0.01$). PB-119 group has the least weight loss, which was a decrease of 16.6% compared with that before administration.

Figure 36:
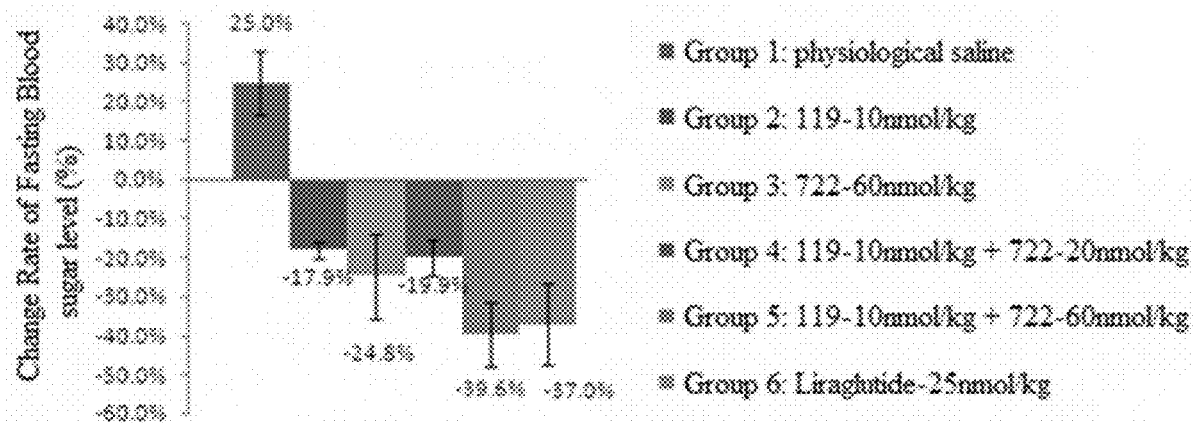
FIG. 36 shows the effect of continuous administration of combination (PB-119+PB-722) for 21 days on the fasting blood sugar level of DIO mice.

Continuous administration of the combination significantly reduced the fasting blood sugar level in the mice. Except that the fasting blood sugar level concentration in the control group increased, the fasting blood sugar level concentration in other treatment groups all decreased to various degrees. The results are shown in FIG. 36. The combination group PB-722 (60 nmol/kg)+PB-119 (10 nmol/kg) had the most significant decrease, which was 39.6% compared with that before administration. The fasting blood sugar level in the liraglutide group (administered twice a day) was reduced by 37.0%. The PB-119 group had the least blood sugar level decrease, which was 17.9% lower than that before administration.

Figure 37:
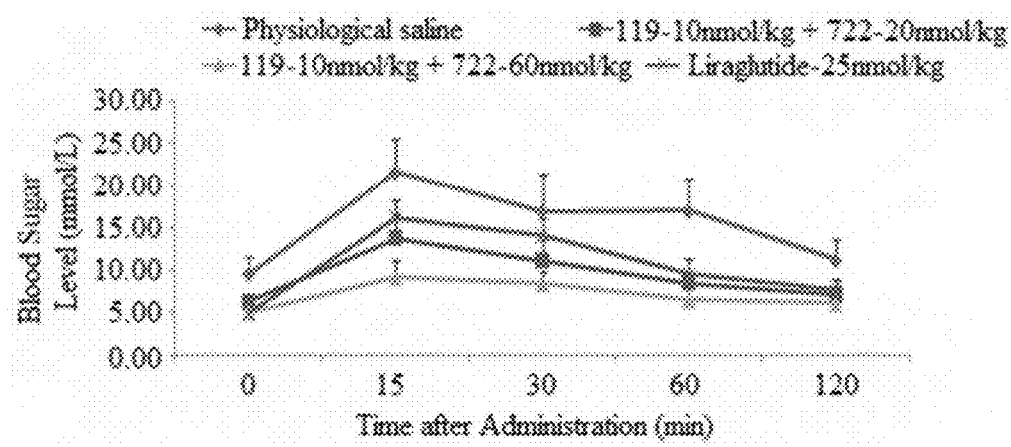
FIG. 37 shows the effect of continuous administration of combination (PB-119+PB-722) for 21 days on oral sugar tolerance of DIO mice.

Continuous administration of the combination also significantly improved oral glucose tolerance in mice. After 21 days of administration, an oral glucose tolerance experiment was performed. Mice were orally given 2.5 g/kg glucose solution, and random glucose level was measured at 0 min, 15 min, 30 min, 60 min and 120 min after sugar feeding. As shown in the results, the area under the blood sugar level concentration-time curve of the high-dose and low-dose combination groups were significantly smaller than that of the control group and significantly better than the liraglutide group, which demonstrated that the combination of the present disclosure effectively improved oral glucose tolerance in mice, and the results are shown in FIG. 37.

Example 21. Experiment for Pharmacological Effect of the Combination of PB-119 and PB-722 in Nonalcoholic Steatohepatitis (NASH) Mouse Model 30 C57/BL6J mice (purchased from Lingchang Biotechnology Co. Ltd., Shanghai, China) were used in this experiment. Twenty four of them were intraperitoneally injected with streptozotocin (STZ) one week after they were born and fed with high-fat diet (purchased from Research Diets, Inc) for five weeks to successfully create a nonalcoholic steatohepatitis (NASH) model. The other 6 were used as normal control and fed with normal diet. The administration started at the sixth week. 24 NASH model mice were randomly divided into 4 groups based on their body weight, 6 mice per group, which were blank control group (0.9% physiological saline), positive control group (10 mg/kg telmisartan), low-dose group (10 nmol/kg PB-119+30 nmol/kg PB-722), high-dose group (10 nmol/kg PB-119+60 nmol/kg PB-722). The positive control group was orally administered once a day and the other groups were administered subcutaneously once every two days for 21 consecutive days. During the administration period, body weight was measured every day and the food intake was measured every two days. After the last day of administration, the animals were fasted overnight, and then weighed and euthanized. Serum and liver tissues were taken and the liver weights were measured. Serum glucose and insulin levels were detected. Liver tissue was fixed with formaldehyde solution, and tissue sections were made and stained with HE, oil red and Sirius red. The sections were examined and scored to determine the NASH index.

Figure 38:
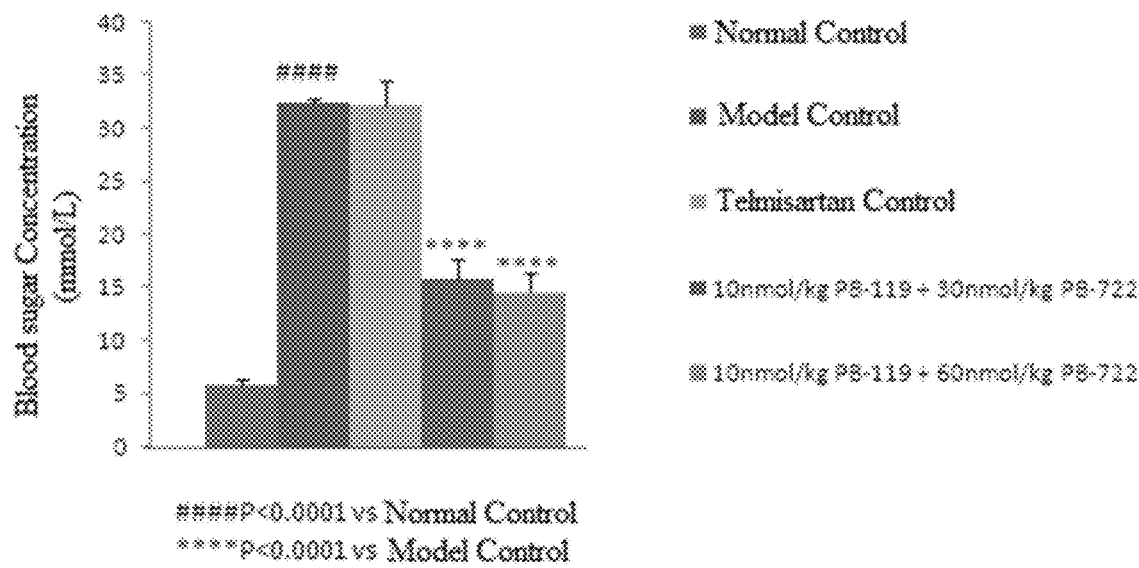
FIG. 38 shows the blood sugar concentration in the mice after continuous administration of combination (PB-119+PB-722) for 21 days.
Figure 39:
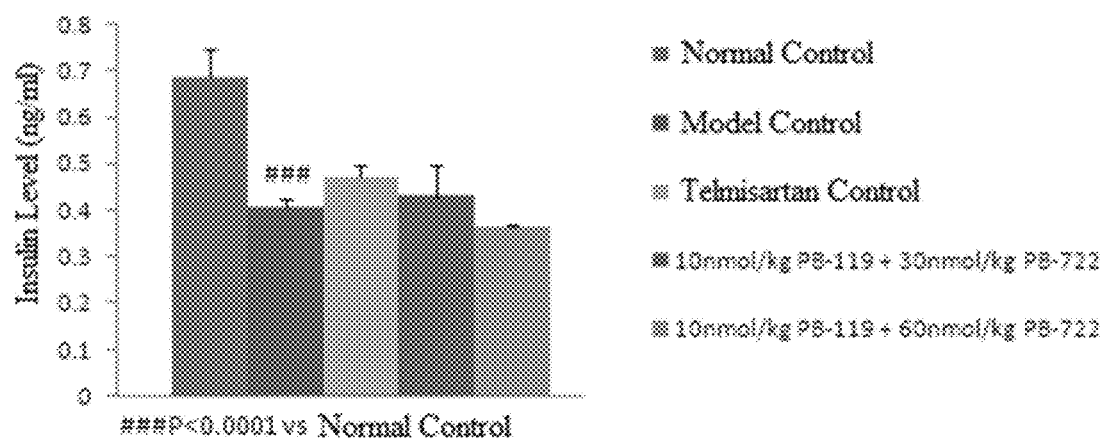
FIG. 39 shows the insulin level in serum of the mice after continuous administration of combination (PB-119+PB-722) for 21 days.

Effect of long-term administration on blood sugar level and insulin levels in mice are shown in FIG. 38 and FIG. 39. The blood sugar level concentration of the model control group was significantly higher than that of the normal control group. The positive control telmisartan had no effect on blood sugar level in animals. After long-term administration of combination low-dose group (10 nmol/kgPB-119+30 nmol/kgPB-722) and high-dose group (10 nmol/kgPB-119+60 nmol/kgPB-722), the blood sugar level concentration decreased significantly, showing an obvious effect on lowering blood sugar level. After long-term administration, there was no significant change in insulin level in each group. Combining this result with the changes in blood sugar level concentration, it was demonstrated that long-term administration of the combination improved insulin sensitivity in animals.

Figure 40:
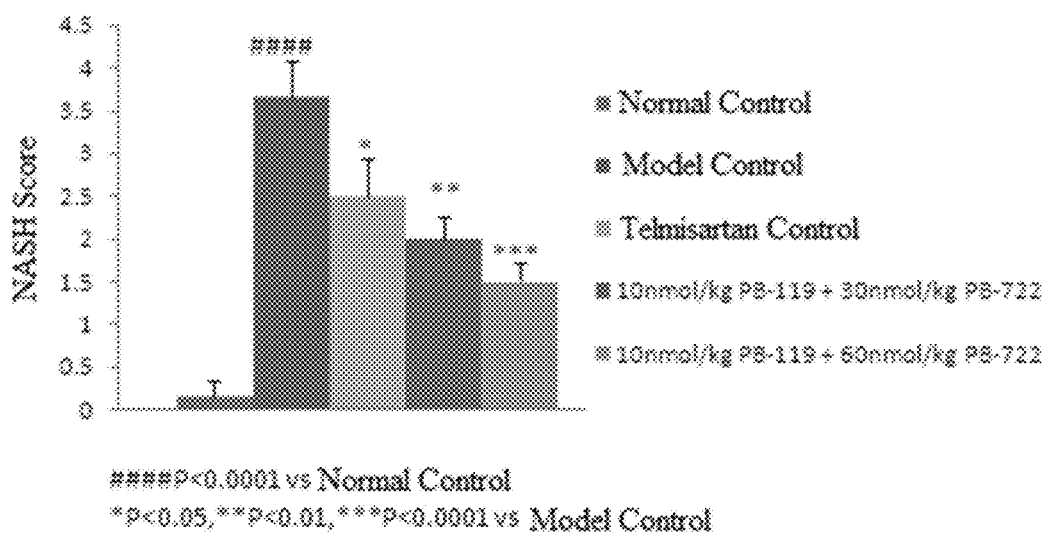
FIG. 40 shows NASH evaluation in the mice after continuous administration of combination (PB-119+PB-722) for 21 days.

After 21 days of continuous administration, NASH scores of the liver sections are shown in FIG. 40. The NASH scores of the model control group were significantly higher than those of normal control group, indicating that the model was successfully established. The long-term administration of PB-119+PB-722 combination improved the NASH score in animals in a dose-dependent manner, indicating that combination administration significantly improved NASH in mice. The NASH scores of the high-dose and low-dose groups were lower than that of the positive control drug, telmisartan.

The above description is only a preferred embodiment, which is by way of example only and does not limit the combination of features necessary for carrying out the present disclosure. The headings provided are not meant to limit the various embodiments of the present disclosure. Terms such as "comprises," "comprising," and "includes" are not intended to be limited. Also, unless specified otherwise, a noun without numeral modification includes plural form, and "or" means "and/or". Unless defined otherwise herein, all technical and scientific terms used herein have the same meaning as commonly understood by one of ordinary skill in the art.

All publications and patents mentioned in this application are incorporated herein by reference. Various modifications and variations of the described methods and compositions of the present disclosure will be apparent to those skilled in the art without departing from the scope and spirit of the present disclosure. Although the present disclosure has been described with specific preferred embodiments, it should be understood that the claimed invention should not be unduly limited to such specific embodiments. Indeed, various modifications of the described embodiments for carrying out the present disclosure which are obvious to those skilled in the art are intended to be within the scope of the claims.

The invention claimed is:

1. A pharmaceutical composition comprising:
   a pharmaceutically effective amount of a glucagon-like peptide-1 (GLP-1) receptor agonist and a glucagon receptor agonist,
   wherein the GLP-1 receptor agonist and the glucagon receptor agonist each independently form a conjugate with a hydrophilic polymer, wherein:
   the GLP-1 receptor agonist is selected from the group consisting of Exendin-4, Exendin-3, GLP-1 and PB-105, and the glucagon receptor agonist is selected from the group consisting of PB-702, PB-703, PB-740 and PB-741, wherein
   PB-105 has the amino acid sequence set forth in SEQ ID NO: 1;
   PB-702 has the amino acid sequence set forth in SEQ ID NO: 3;
   PB-703 has the amino acid sequence set forth in SEQ ID NO: 4;
   PB-740 has the amino acid sequence set forth in SEQ ID NO: 5; and
   PB-741 has the amino acid sequence set forth in SEQ ID NO: 6;
   the hydrophilic polymer is a polyethylene glycol (PEG); and
   the molar ratio of the GLP-1 receptor agonist to the glucagon receptor agonist is 1:3 to 1:10.

2. The pharmaceutical composition according to claim 1, which further comprises a pharmaceutically acceptable carrier.

3. The pharmaceutical composition according to claim 1, wherein the polyethylene glycol has a molecular weight of 2 kDa to 60 kDa, 5 kDa to 50 kDa, 10 kDa to 40 kDa, 20 kDa to 40 kDa, 15 kDa to 30 kDa, or 21 kDa to 29 kDa.

4. The pharmaceutical composition according to claim 1, comprising an item selected from the group consisting of: combination of PB-721 and PB-119, combination of PB-722 and PB-119 and combination of PB-708 and PB-120, wherein:
   PB-721 is mPEG-23KD-ppMAL-PB-740, wherein PB-740 has an amino acid sequence of SEQ ID NO: 5;
   PB-722 is mPEG-23KD-ppMAL-PB-741, wherein PB-741 has an amino acid sequence of SEQ ID NO: 6;
   PB-119 is mPEG-23KD-ppMAL-PB-105, wherein PB-105 has an amino acid sequence of SEQ ID NO: 1;
   PB-120 is mPEG-25KD-ppMAL-PB-105, wherein PB-105 has an amino acid sequence of SEQ ID NO; and
   PB-708 is mPEG-25KD-ppMAL-PB-703, wherein PB-703 has an amino acid sequence of SEQ ID NO: 4.

5. A kit, comprising the composition according to claim 1, and instruction for use.

6. A method for treating nonalcoholic fatty liver disease, losing weight, lowering lipid level, lowering blood sugar level, inhibiting appetite, lowering serum total cholesterol level and/or reducing triglyceride content in the liver in a subject in need thereof, comprising administering the composition according to claim 1 to the subject.

\* \* \* \* \*